US006555566B2

(12) United States Patent
Ponikau

(10) Patent No.: US 6,555,566 B2
(45) Date of Patent: *Apr. 29, 2003

(54) METHODS AND MATERIALS FOR TREATING AND PREVENTING INFLAMMATION OF MUCOSAL TISSUE

(75) Inventor: Jens Ponikau, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/865,785

(22) Filed: May 25, 2001

(65) Prior Publication Data

US 2001/0031779 A1 Oct. 18, 2001

Related U.S. Application Data

(63) Continuation of application No. 09/177,273, filed on Oct. 22, 1998, now Pat. No. 6,291,500.
(60) Provisional application No. 60/086,397, filed on May 22, 1998, provisional application No. 60/083,272, filed on Apr. 28, 1998, provisional application No. 60/063,418, filed on Oct. 28, 1997, provisional application No. 60/063,414, filed on Oct. 28, 1997, and provisional application No. 60/062,709, filed on Oct. 22, 1997.

(51) Int. Cl.$^7$ ...................... A61K 31/415; A61K 31/70; A61K 31/41; A61K 31/34; A61K 31/20
(52) U.S. Cl. ................. 514/393; 514/31; 514/282; 514/394; 514/462; 514/560
(58) Field of Search ................ 514/393, 31, 282, 514/394, 462, 560

(56) References Cited

U.S. PATENT DOCUMENTS

| | | | |
|---|---|---|---|
| 3,929,992 A | 12/1975 | Sehgal et al. ............. 424/122 |
| 3,991,750 A | 11/1976 | Vickery | |
| 4,209,447 A | 6/1980 | Heeres ............... 260/340.9 R |
| 4,334,538 A | 6/1982 | Juhn | |
| 4,402,957 A | 9/1983 | Heeres et al. ............. 424/250 |
| 4,432,991 A | 2/1984 | Dusza et al. ............. 424/273 P |
| 4,883,785 A | 11/1989 | Chow et al. | |
| 4,916,134 A | 4/1990 | Heeres et al. ............. 514/252 |
| 5,075,309 A | 12/1991 | Heeres et al. ............. 514/252 |
| 5,080,899 A | 1/1992 | Sturm et al. ............. 424/122 |
| 5,248,504 A | 9/1993 | Friedman ................ 424/434 |
| 5,310,545 A | 5/1994 | Eisen ..................... 424/49 |
| 5,441,977 A | 8/1995 | Russo et al. .............. 514/411 |
| 5,487,739 A | 1/1996 | Aebischer et al. | |
| 5,582,167 A | 12/1996 | Joseph | |
| 5,614,206 A | 3/1997 | Randolph et al. | |
| 5,654,293 A | 8/1997 | Francois et al. ............ 514/171 |
| 5,658,881 A | 8/1997 | Gelland et al. ............. 514/11 |
| 5,707,975 A | 1/1998 | Francois et al. ............ 514/58 |
| 5,756,127 A | 5/1998 | Grisoni et al. | |
| 5,897,872 A | 4/1999 | Picciano ................ 424/434 |
| 6,207,703 B1 * | 3/2001 | Ponikau ................ 514/460 |
| 6,291,500 B2 * | 9/2001 | Ponikau ................ 514/393 |

FOREIGN PATENT DOCUMENTS

| | | |
|---|---|---|
| RU | 2 128 053 | 3/1999 |
| RU | 2 139 707 | 10/1999 |
| WO | WO 94/05265 | 3/1994 |
| WO | WO 95/08993 | 4/1995 |
| WO | WO 97/03651 | 2/1997 |
| WO | WO 97/17078 | 5/1997 |
| WO | WO 99/38459 | 8/1999 |

OTHER PUBLICATIONS

Medline Abstract, AN 76164576, 1976, Torpoco et al.*
Corey JP et al., "Fungal diseases of the sinuses," *Otolaryngology—Head and Neck Surgery* 103:1012–1015 (1990).
"Guidelines for the Diagnosis and Management of Asthma," Expert Panel Report 2, NIH Publication No. 97–4051, pp. i–ix, 1–146, Jul., 1997.
Haria et al., et al., *Published Erratum in Drugs,* 52(2):253 (1996).
Kauffman HF et al., "Review of Fungus–induced Asthmatic Reactions," *Am. J. Respir. Crit. Care Med.* 151:2109–2116 (1995).
Martinez–Berriotxoa A et al., Medline Abstract 97323779 (1997).
Torpoco JO et al., Medline Abstract 76164576 (1976).
Updated Substantive U.S. Patent and Trademark Office correspondence for U.S. Application Serial No. 09/177,164 from Jul. 4, 2002 up to and including Oct. 1, 2002.
Vaughan LM, "Allergic bronchopulmonary aspergillosis," *Clin. Pharm.*, 12:24–33 (1993).
Zhaoming W and Lockey RF, "A review of allergic bronchopulmonary aspergillosis," 6(3):144–151 (1996).
Substantive U.S. Patent and Trademark Office correspondence for U.S. Application Serial No. 09/177,164 up to and including Jul. 3, 2002.
Sobolev et al., "Role of antimycotic therapy in treating of bronchial asthma," Russian National Congr., People and Drug, Moscow, 8–12.04–97.

(List continued on next page.)

Primary Examiner—Kevin E. Weddington
(74) Attorney, Agent, or Firm—Fish & Richardson P.C., P.A.

(57) ABSTRACT

The invention involves methods and materials for treating and preventing non-invasive fungus-induced mucositis. Specifically, the invention involves administrating an antifungal agent such that it contact mucus in an amount, at a frequency, and for a duration effective to prevent, reduce, or eliminate non-invasive fungus-induced rhinosinusitis. This invention also provides methods and materials for diagnosing non-invasive fungus-induced rhinosinusitis and culturing non-invasive fungus from a mammalian mucus sample as well as specific antifungal formulations and medical devices for treating and preventing non-invasive fungus-induced rhinosinusitis. In addition, the invention provides methods and materials for treating and preventing other non-invasive fungus-induced mucositis conditions such as chronic otitis media, chronic colitis, and Crohn's disease. Further, the invention involves methods and materials for treating and preventing chronic asthma symptoms.

46 Claims, 2 Drawing Sheets

OTHER PUBLICATIONS

Adam et al., *Medicine,* 1986, 65(4):203–217.
Akiyama et al., *Allergy,* 1996, 51(12):887–892.
Allphin et al., *Laryngoscope,* 1991, 101(8):815–820.
Arrese et al., *J. Med. Vet. Mycol.,* 1995, 33(2):127–130.
Bartynski et al., *Otolaryngol. Head Neck Surg.,* 1990, 103:32–39.
Bassiouny et al., *J. Laryngol. Otol.,* 1982, 96:215–228.
Baumjohann et al., *TW Gynakologie,* 1999, 4:400–402.
Becelli et al., *Niverva Stomatologica,* 1995, 44:171–174.
Bent et al., *Allergy and Asthma Proc.,* 1996, 17(5):259–268.
Bent and Kuhn, *Otolaryngol. Head Neck Surg.,* 1994, 111:580–588.
Bent and Kuhn, *Laryngoscope,* 1996, 106:1331–1334.
Berman et al., *J. Allergy Clin. Immunol.,* 1974, 53(5):311–317.
Berrettini et al., *Acta Otohinolaryngol. Ital.,* 1996, 16:447–454.
Birnbaum et al., *J. Am. Acad. Sermatol.,* 1990, 23(4, Part 2):782–785.
Black, *Proc. Roy. Soc. Med.,* 1960, 53:974–975.
Breuer et al., *Digestive Diseases and Sciences,* 1991, 36(2):185–187.
Bullock et al., *Am. J. Ophthalmology,* 1974, 78(5):811–815.
Busch, *Arch. Intern. Med.,* 1994, 154(7):815–819.
"Cases of Pulmonary Mycosis in Compromised Hosts" 1975.
Cayton et al., *The Lancet,* 1974, pp. 303–307.
Chakrabarti et al., *Advances in Medical Mycology,* 1997, 2:39–59.
Chapman et al., *Gut,* 1994, 35(1):73–76.
Clark et al., *J. Infection,* 1996, 32:147–150.
Cody et al., *Laryngoscope,* 1994, 104:1074–1079.
Cody et al., *Rhinologic Diagnosis and Treatment,* Chapter 15, pp. 317–333 1995.
Cohen, *Ann. Otol. Rhinol. Laryngol.,* 1990, 99:427–431.
"Combining Hydrocortisone with an Antifungal on the Skin," *Drug and Therapeutics Bulletin,* 1985, 23(21):83–84.
Corey et al., *Otolaryngol. Head Neck Surg.,* 1995, 113:110–119.
Costa et al., *JAMA,* 1997, 278(22):1815–1822.
Cox et al., *J. Clin. Microbiol.,* 1994, 32(9):2301–2304.
Cross, *Chest,* 1995, 108:599–601.
De Carpentier et al., *J. Laryngol. Otol.,* 1994, 314–318.
De Guademar et al., *Ann. Oto–Laryng. (Paris),* 1993, 110:198–202.
Degreef, *Annales de Dermatologie et de Venereologie,* 1993, 120:21–31.
Demaerel et al., *British J. Radiol.,* 1993, 66:260–263.
Denning et al., *Chest,* 1991, 100:813–819.
deShazo and Swain, *J. Allergy Clin. Immunol.,* 1995, 96:24–35.
deShazo et al., *J. Allergy Clin. Immunol.,* 1997, 99(4):475–485.
deShazo et al., *New England J. Med.,* 1997, 337(4):254–259.
Dhindsa et al., *J. Med. Vet. Mycol.,* 1995, 33:59–61.
Diehl, *Am. Fam. Physician,* 1996, 54(5):1687–1692.
Dubois et al., *Chest,* 1995, 108:750–753.
Dunand et al., *Clin. Infect. Diseases,* 1997, 25:267–272.
Edwards et al., *Lancet,* 1964, 1:1349–1353.
Ence et al., *Am. J. Rhinology,* 1990, 4(5):169–178.
Falser, *Dermatologica,* 1984, 169(1):135–140.
Farquhar et al., *Scott Med. J.,* 1984, 29:192–193.

Favre et al., *Antimicrobial Agents and Chemotherapy,* 1996, 40(2):443–447.
Feger et al., *Annals of Allergy, Asthma & Immunology,* 1997, 79:221–225.
Fournier, *Thorax,* 1987, 42:831.
Friedman et al., *Am. J. Clin. Pathol.,* 1991, 96:368–372.
Germaud and Tuchais, *Chest,* 1995, 107:883.
Goldsten, *Hospital Practice,* 1992, pp. 73–74, 79–81, 83–84, 87–88, 91–92.
Haneke, *Z. Hautkr.,* 1982, 57(16):1165–1176.
Haria et al., *Drugs,* 1996, 51(4):585–620.
Harig et al., *New England J. Med.,* 1989, 320(1):23–28.
Harlin et al., *J. Allergy Clin. Immunol.,* 1988, 81 (5, Part 1):867–875.
Heier et al., *Ophthalmology,* 1995, 102(5):713–717.
Horner et al, *Clin. Microbial. Rev.,* 1995, 8(2):161–179.
Hussain et al., *J. Pharm. Sci.,* 1984, 73(7):1300–1301.
Ismail et al., *Arch. Intern. Med.,* 1993, 153:1604–1606.
Jacobson et al., *Clin. Neuro–ophthalmol.,* 1992, 12(4):250–256.
Jonathan et al., *J. Laryngol. Otol.,* 1989, 103:1181–1183.
Kaliner et al., *Otolaryngol. Head Neck Surg.,* 1997, 11(6, Part 2):S1–S20.
Katzenstein et al., *J. Allergy Clin. Immunol.,* 1983, 72(1):89–93.
Kilburn, "The Innocuousness and Possible Therapeutic Use of Aerosol Amphotericin–B," U.S. Army Medical Research & Nutrition Laboratory, Fitzsimmons Army Hospital, Denver, Colorado, 1959, pp. 441–442.
Kinsella et al., *Clin. Otolaryngol.,* 1996, 21:389–392.
Kintzel et al., *Ann. Pharmacother.,* 1994, 28(3):333–335.
Kudo et al., *Kekkaku (Japan),* 1997, 72(2):31–38.
Kupferberg et al., *Arch. Otolaryngol. Head Neck Surg.,* 1996, 122:1381–1384.
Kupferberg et al., *Otolaryngol. Head Neck Surg.,* 1997, 117:35–41.
LeBeau et al., *Mycoses,* 1994, 37:171–179.
Lemanske et al., *JAMA,* 1997, 278(2):1855–1873.
Mabry et al., *Otolaryngol. Head Neck Surg.,* 1995, 113(6):721–723.
Mabry et al., *Otolaryngol. Head Neck Surg.,* 1997, 116(1):31–35.
MacMillan et al., *Hum. Pathol.,* 1987, 18:960–964.
Manning et al., *Arch. Otolaryngol. Head Neck Surg.,* 1991, 117:174–178.
Marriott et al., *Dermatologica,* 1983, 166(Suppl. 1):1–7.
Maskin et al., *Ophthalmology,* 1989, 96:175–179.
Mathews et al., *Veterinary Surgery,* 1996, 25:309–319.
McKendrick et al., *Lancet,* 1958, pp. 621–622.
McKendrick and Medlock, *Lancet,* 1958, pp. 1229–1230.
Meyer et al., *Medicine,* 1994, 73(2):69–78.
Morgan et al., *Am. J. Clin. Pathol.,* 1984, 82(5):597–601.
Morpeth et al., *Annals of Allergy, Asthma & Immunology,* 1996, 76:128–136, 139–140.
Muntz et al., *Otolaryngologic Clinics of North America,* 1996, 29(1):185–192.
Negroni et al., *Arch. Med. Res.,* 1993, 24(4):387–393.
Nicolau et al., *Ann. Pharmacother.,* 1995, 29:994–996.
Nishioka et al., *Otolaryngol. Head Neck Surg.,* 1994, 110(6):494–500.
Nolting et al., *Firtschritte der Medizin,* 1998, 115:22–28.
Nouri, *Laryngologie Rhinologie Otologie,* 1986, 65(8):420–422.

Ogawa, *Japanese Society for Tuperculosis,* (Kekkaku), 1997, 72(2):59–64.
Pasha et al., *Gastroenterology,* 1997, 112:250–254.
Philip and Keen, *Brief Report,* 1988, 14(2):222–224.
Phillips et al., *Otolaryngol. Head Neck Surg.,* 1987, 96(6):577–579.
Piantoni et al., *Clin. Ter.,* 1989, 130:23–27.
Pingree et al., *Otolaryngol. Head Neck Surg.,* 1992, 106(3):302–305.
Ponikau et al., "Chronic sinusitis/polyposis secondary to fungal organisms," *Submitted to 43rd Annual Meeting of the American Rhinologic Society,* Sep. 6, 1997, San Francisco, California.
Purcell and Corris, *Thorax,* 1995, 50:1321–1323.
Quraishi et al., *Otolaryngol. Head Neck Surg.,* 1997, 117:29–34.
Ramos et al., "Oral administration of short–chain fatty acids reduce the intestinal mucositis caused by treatment with Ara–C in mice fed commercial or elemental diets," 1997, Abstract.
Ramos et al., *Nutrition and Cancer,* 1997, 28(2):212–217.
Robb, *J. Laryngology and Otology,* 1986, 100:1071–1077.
Robson et al., *Aust. NZ J. Med.,* 1989, 19:351–353.
Roithmann et al., *Rhinology,* 1995, 33:104–110.
Rolston et al., *Reviews of Infectious Diseases,* 1985, 7(4):525–529.
Roth, *Ear, Nose & Throat J.,* 1994, 73:928–930.
Sait et al., *Digestive Diseases,* 1970, 15:993–1002.
Schaffner, *Schweiz. Med. Wschr.,* 1991, 121:1413–1418.
Schubert et al., *Z. Hautkr.,* 1984, 59(24):1681–1682, 1685–1686.
Schwartz, *Annals of Allergy, Asthma & Immunology,* 1996, 77:500–502.
Schwietz et al., *Allergy Proc.,* 1992, 13(1):3–6.
Shale et al., *Thorax,* 1987, 42:26–31.
Shen et al., *Clin. Exp. Allergy,* 1996, 26(4):444–451.
Slavin et al., *J. Allergy,* 1970, 46(3):150–155.
Slavin, *JAMA,* 1997, 278(22):1849–1854.
Soyinka, *Curr. Med. Res. Opin.,* 1987, 10(6):390–396.
Stark, *Diseases of the Chest,* 1967, 51(1):96–99.
Stettendorf, *Arzneimittel Forschung (Drug Research ),* 1983, 33(5):750–754.
Stool, *AFP,* 1985, 32(6):101–107.
Swift et al., *J. Laryngology and Otology,* 1998, 112:92–97.
Tariq et al., *Clin. Exp. Allergy,* 1996, 26(7):794–798.
Tiwari et al., *Mycoses,* 1995, 38:297–300.
Torres et al., *Hum. Pathol.,* 1996, 27(8):793–799.
Tosti et al., *Pediatric Dermatology,* 1997, 14(2):146–148.
Travis et al., *Hum. Pathol.,* 1991, 22(12):1240–1248.
Tsushima et al., *Internal Medicine,* 1996, 35(9):736–741.
Urakami et al., "Clnical Features of Eight Cases of Opporunistic fungal Pneumonias," Fourth Department of Internal Medicine, Kinki University School of Medicine, Osakasayama, Japan 1984.
Van Cutsem *Mycoses,* 1989, 32(1):14–34.
Vanden Bossche et al., *Am. J. Obstet. Gynecol.,* 1991, 165(4, Part 2):1193–1199.
Waitzman et al., *J. Otolaryngol.,* 1994, 23(4):244–249.
Washburn et al., *Medicine,* 1988, 67(4):231–247.
Waxman et al., *Laryngoscope,* 1987, 97:261–266.
Wengrower et al., *Respiration,* 1985, 47:209–213.
Zieske et al., *Otolaryngol. Head Neck Surg.,* 1991, 105(4):567–577.

* cited by examiner

METHODS AND MATERIALS FOR TREATING AND PREVENTING INFLAMMATION OF MUCOSAL TISSUE

CROSS REFERENCE TO RELATED APPLICATIONS

This application is a continuation of U.S. application Ser. No. 09/177,273, filed Oct. 22, 1998 is now 6291500. In addition, this application claims priority from U.S. application Ser. No. 09/177,273, filed Oct. 22, 1998, U.S. Provisional Patent Application Serial No. 60/062,709, filed Oct. 22, 1997, U.S. Provisional Patent Application Serial No. 60/063,414, filed Oct. 28, 1997, U.S. Provisional Patent Application Serial No. 60/063,418, filed Oct. 28, 1997, U.S. Provisional Patent Application Serial No. 60/083,272, filed Apr. 28, 1998 and U.S. Provisional Patent Application Serial No. 60/086,397, filed May 22, 1998.

BACKGROUND

1. Technical Field

The invention relates to methods and materials involved in the treatment and prevention of non-invasive fungus-induced inflammation of mucosal tissue as well as asthma symptoms.

2. Background Information

Mucositis, the inflammation of mucosal tissue, is a serious medical problem that affects millions of people worldwide. For example, conservative estimates indicate that between 20 to 40 million Americans suffer from chronic rhinosinusitis, an inflammation of the nasal cavity and/or paranasal sinuses.

For the most part, the cause of chronic rhinosinusitis is unknown. In a small percentage of patients, however, non-invasive fungal organisms living within mucus seem to be involved. Patients having this condition, now known as allergic fungal sinusitis (AFS), were first described in the early 1980's (Miller J W et al., *Prod. Scot. Thor. Soc.* 36:710 (1981) and Katzenstein A L A et al., *J. Allergy Clin. Immunol.* 72:89–93 (1983)). Specifically, about three to eight percent of chronic rhinosinusitis cases requiring surgery because of nasal obstruction caused by polyp formation have been classified as AFS. Briefly, AFS is diagnosed by the presence of inspissated mucus in the nasal-paranasal cavities. Typically, this mucus contains clumps or sheets of necrotic eosinophils, Charcot-Leyden crystals, and non-invasive fungal hyphae. In addition, patients with AFS typically have a history of nasal-paranasal polyposis and may have undergone multiple surgeries. Inflammation can affect all nasal-paranasal cavities, but also can be asymmetric involving only one side. Computed topography (CT) scans of patients with AFS have a characteristic appearance and often reveal bone erosion in adjacent structures. Indeed, destruction of bones adjacent to the sinuses and nasal areas ranging from 19 percent to 80 percent has been reported.

Although fungal organisms seem to be the causative agent of AFS, successful treatment remains lacking. Currently, AFS patients as well as most chronic rhinosinusitis patients receive surgical treatment with or without steroid therapy. Surgery helps clear the nasal-paranasal cavities when obstructed by polyps and steroid therapy helps control inflammatory responses that seem to be causing tissue and bone destruction. Unfortunately, patients treated with surgery alone almost always experience recurrent rhinosinusitis symptoms and additional polyp growth. In addition, prolonged use of steroids is associated with significant side effects and steroid therapy removal also leads to recurrent episodes of rhinosinusitis. For these reasons, people suffering from chronic rhinosinusitis conditions typically experience repeated cycles of intense inflammation, surgery, and steroid therapy followed by recurrent intense inflammation. Thus, neither surgery nor steroid therapy is particularly effective or desirable as a long-term treatment for chronic rhinosinusitis conditions.

SUMMARY

The present invention relates generally to methods and materials for treating and preventing non-invasive fungus-induced mucositis. The term "mucositis" as used herein means an inflammation, as opposed to an infection, of a mucus membrane. This invention is based on the discovery that the condition known as AFS can be treated successfully by using an antifungal agent in an amount, at a frequency, and for a duration effective to reduce inflammation caused by the presence of fungal organisms within nasal-paranasal mucus. In addition, this invention is based on the discovery that using an antifungal agent in an amount, at a frequency, and for a duration effective to maintain a reduced level of fungal organisms within nasal-paranasal mucus can prevent AFS symptoms. Specifically, the invention involves administering an antifungal agent to a mammal such that the antifungal agent contacts the mammal's mucus and reduces the presence of fungal organisms in mucus. In addition to being the only known method for successfully treating and preventing AFS, the use of an antifungal agent is particularly advantageous to a patient when compared to other currently available medical approaches to AFS such as surgical treatments and steroid therapies. Such medical approaches can have side effects, can be costly, and may be associated with patient discomfort.

This invention is also based on the discovery that most, if not all, chronic rhinosinusitis conditions have a fungal etiology and that most, if not all, cases of chronic rhinosinusitis can be treated by using an antifungal agent in an amount, at a frequency, and for a duration effective to reduce the presence of fungal organisms within nasal-paranasal mucus. In addition, using an antifungal agent in an amount, at a frequency, and for a duration effective to maintain a reduced level of fungal organisms within nasal-paranasal mucus can prevent chronic rhinosinusitis symptoms.

This discovery is contrary to the current understanding of chronic rhinosinusitis and has far-reaching implications within medicine. For example, numerous medical research articles report that about three to eight percent of chronic rhinosinusitis cases requiring surgery are AFS, a rhinosinusitis condition having a non-invasive fungal etiology. In fact, less than 150 cases of AFS have been reported in the literature over the past 15 years. It is noted that the lack of appreciation for the non-invasive fungal etiology of chronic rhinosinusitis conditions may have occurred since affected individuals are frequently found to have bacterial infections (i.e., invasive bacteria). Presumably, tissue damage caused by non-invasive fungus-induced inflammation results in a higher occurrence of bacterial infections in those damaged areas. Thus, overlaying bacterial infections in affected individuals could have masked the underlaying cause, fungal organisms within mucus.

For the purpose of this invention, the term "non-invasive fungus-induced rhinosinusitis" includes AFS as well as any other nasal-paranasal mucositis condition having a non-invasive fungal etiology.

Treating and preventing non-invasive fungus-induced rhinosinusitis, whether diagnosed as AFS or any other rhinosinusitis condition having a non-invasive fungal etiology, by using an antifungal agent circumvents the need for surgical treatments and steroid therapies that cause significant pain and suffering to the patient. Moreover, the use of antifungal agents to treat and prevent non-invasive fungus-induced rhinosinusitis actually directs treatment against the etiological agent (i.e., fungus), unlike surgical treatments, steroid therapies, and antibacterial treatments.

The term "chronic" as used herein refers to afflictions present for at least three months. It is to be understood that afflictions that are treated as described herein and become asymptomatic can be classified as chronic. Thus, chronic afflictions can be symptomatic or asymptomatic.

This invention is also based on another, equally significant, discovery that chronic asthma symptoms can be treated and prevented successfully by using an antifungal agent in an amount, at a frequency, and for a duration effective to reduce the presence of fungal organisms within airway mucus. It is also apparent from the present discoveries that antifungal agents can be administered directly to the lung airways for the treatment of chronic asthma. Again, these discoveries are contrary to the current understanding of chronic asthma and have far-reaching clinical implications. Taken together, these significant breakthroughs can potentially allow large populations to experience happier, healthier, and more productive daily lives.

Specifically, the invention provides methods and materials for treating and preventing a wide variety of mucoinflammatory diseases by using an antifungal agent. The use of an antifungal agent is a safe and highly effective treatment approach that involves mucoadministering an antifungal agent in an amount, at a frequency, and for a duration effective to reduce, prevent, or eliminate a non-invasive fungus-induced mucositis. The term "mucoadministration" as used herein refers to any type of administration that places an administered agent in contact with mucus. This invention also provides specific antifungal formulations that can be applied to the various parts of a mammal that contain mucus. In addition, the invention provides medical devices that can be used to apply antifungal formulations. These devices are particularly advantageous since they can be used by an individual to administer an effective dose of a specific antifungal formulation to the appropriate area of the body. Further, the invention provides improved methods and materials for collecting and culturing fungal organisms from mucus samples. These culturing techniques can be used to monitor the number of fungal species within mucus during a particular antifungal treatment regimen. In addition, these fungus collecting and culturing methods and materials are useful for identifying the genotype and phenotype of specific fungal organisms that cause non-invasive fungus-induced mucositis. The identification and characterization of non-invasive fungal organisms found in a particular individual's mucus can assist clinicians in determining proper treatment and prophylactic approaches. For example, this information can help determine the specific antifungal agent, amount, mode of administration, and number of applications to be used as well as possible combinatorial therapies that may include other medications and procedures such as steroids, antibacterial agents, and surgery.

In general, the invention features a method for treating a mammal (e.g., human) having non-invasive fungus-induced rhinosinusitis. This method involves directly mucoadministering to at least a portion of the mammal's nasal-paranasal anatomy a formulation in an amount, at a frequency, and for a duration effective to reduce or eliminate non-invasive fungus-induced rhinosinusitis. This formulation contains an antifungal agent or a plurality of antifungal agents and can be in a solid, liquid, or aerosol form (e.g., a powder, crystalline substance, gel, paste, ointment, salve, cream, solution, suspension, partial liquid, spray, nebulae, mist, atomized vapor, aerosol, and tincture). In addition, the formulation can be in a form suitable for self-mucoadministration by a human.

Further, the formulation can contain a pharmaceutically acceptable aqueous vehicle (e.g., saline and water). For example, a liquid form of the formulation can contain about 0.00001 percent to about 20 percent of an antifungal agent as determined by antifungal agent weight per aqueous vehicle volume. In addition, the formulation can contain about 0.01 ng to about 1000 mg of an antifungal agent (e.g., amphotericin B) per liter in some embodiments of the invention, or about 1 ng to about 500 mg of an antifungal agent per liter in other embodiments of the invention, or about 100 mg of an antifungal agent per liter in still other embodiments of the invention. In addition, an effective amount of these aqueous formulations can be about 0.01 mL to about 1 L of formulation per nostril in some embodiments of the invention, or about 5 mL to about 100 mL of formulation per nostril in other embodiments of the invention, or about 40 mL of formulation per nostril in still other embodiments of the invention. Alternatively, an effective amount of a formulation can be about 0.01 ng to about 1000 mg of an antifungal agent per kg of body weight of the mammal in some embodiments of the invention or about 1 ng to about 500 mg of an antifungal agent per kg of body weight of the mammal in other embodiments of the invention. The effective amount of a formulation can change or remain the same during an effective duration. The effective frequency of direct mucoadministration can be from about four times a day to about once every other week in some embodiments of the invention, or from about twice a day to about once a week in other embodiments of the invention, or about twice a day in still other embodiments of the invention. In addition, the effective frequency of direct mucoadministration can be greater than once a day, or greater than once a week. The effective duration can be greater than about 7, 14, 30, 60, or 90 days.

The mammal can be atopic or nonatopic and can be immunocompetent or immunocompromised. In addition, the non-invasive fungus-induced rhinosinusitis can be characterized by polyp formation or polypoid change. The non-invasive fungus-induced rhinosinusitis also can be a chronic condition. Mucoadministration can be an irrigation of at least a portion of the nasal-paranasal anatomy with a liquid form of the formulation. Alternatively, the mucoadministration can involve applying an aerosol form of the formulation to at least a portion of the nasal-paranasal anatomy. An antifungal agent can be in a solid, liquid, or aerosol form. In addition, an antifungal agent can be a polyene macrolide, tetraene macrolide, pentaenic macrolide, fluorinated pyrimidine, imidazole, azole, triazole, halogenated phenolic ether, thiocarbamate, allylamine, sterol inhibitor, and an agent that interpolates fungal cell wall components. Such antifungal agents include amphotericin B, flucytosine, ketoconazole, miconazole, itraconazole, fluconazole, griseofulvin, clotrimazole, econazole, terconazole, butoconazole, oxiconazole, sulconazole, saperconazole, voriconazole, ciclopirox olamine, haloprogin, tolnaftate, naftifine, terbinafine hydrochloride, morpholines, nystatin, natamycin, butenafine, undecylenic acid, Whitefield's ointment, propionic acid, and caprylic acid. In addition to containing an antifungal agent, the formulation can contain, without limitation, a pharmaceutically acceptable aqueous vehicle, pharmaceutically acceptable solid vehicle, steroid, mucolytic agent, antibacterial agent, anti-inflammatory agent, immunosuppressant, dilator, vaso-constrictor, decongestant, leukotriene inhibitor, anti-cholinergic, anti-histamine, therapeutic compound, and combinations thereof.

The method can also involve administering a second formulation that contains, without limitation, an antifungal agent, antibacterial agent, steroid, mucolytic agent, anti-inflammatory agent, immunosuppressant, dilator, vaso-constrictor, decongestant, leukotriene inhibitor, anti-cholinergic, anti-histamine, therapeutic compound, or combination thereof. Likewise, the method can involve an additional step after the direct mucoadministration. This additional step can be a prophylactic mucoadministration of a prophylactic formulation to the mammal in an amount, at a frequency, and for a duration effective to prevent non-invasive fungus-induced rhinosinusitis. This prophylactic formulation also contains an antifungal agent and can be in a solid, liquid, or aerosol form (e.g., powder, crystalline substance, gel, paste, ointment, salve, cream, solution, suspension, partial liquid, spray, nebulae, mist, atomized vapor, aerosol, tincture, pill, capsule, tablet, and gelcap). In addition, the prophylactic mucoadministration can be a direct or indirect mucoadministration. For example, the prophylactic mucoadministration can be an irrigation of at least a portion of the nasal-paranasal anatomy with a liquid form of the prophylactic formulation, an application of an aerosol form of the prophylactic formulation to at least a portion of the nasal-paranasal anatomy, or an oral administration of the prophylactic formulation to the mammal in the form of a solid or liquid.

It will be understood that each of the additional features of the invention described above can be applied to the following additional embodiments and aspects of the invention. For example, methods for prophylactically treating a mammal at risk for developing non-invasive fungus-induced rhinosinusitis, and methods for treating asthma, may utilize a formulation in which the antifungal agent is about 0.00001 percent to about 20 percent by weight or volume of a formulation, and so forth.

In another embodiment, the invention features a method for prophylactically treating a mammal at risk for developing non-invasive fungus-induced rhinosinusitis. This method involves mucoadministering to the mammal a formulation in an amount, at a frequency, and for a duration effective to prevent non-invasive fungus-induced rhinosinusitis. This formulation contains an antifungal agent.

Another embodiment of the invention features a method for treating a mammal having non-invasive fungus-induced rhinosinusitis. This method involves the steps of identifying (e.g., diagnosing) the mammal, and directly mucoadministering a formulation to at least a portion of the nasal-paranasal anatomy of the mammal in an amount, at a frequency, and for a duration effective to reduce or eliminate non-invasive fungus-induced rhinosinusitis. This formulation contains an antifungal agent.

Another embodiment of the invention features a method for prophylactically treating a mammal at risk for developing non-invasive fungus-induced rhinosinusitis. This method involves the steps of identifying the mammal (e.g., diagnosing), and mucoadministering a formulation to at least a portion of the nasal-paranasal anatomy of the mammal in an amount, at a frequency, and for a duration effective to prevent non-invasive fungus-induced rhinosinusitis. This formulation contains an antifungal agent.

In another aspect, the invention features a method for treating a mammal having asthma. This method involves directly mucoadministering to at least a portion of the airways (e.g., nasal-paranasal airways and lung airways) of the mammal a formulation in an amount, at a frequency, and for a duration effective to reduce or eliminate asthma symptoms. This formulation contains an antifungal agent. The direct mucoadministration can be the irrigation of the nasal-paranasal anatomy of the mammal with a liquid form of the formulation. Alternatively, the direct mucoadministration can be the inhalation of the formulation through the mammal's mouth or nose. In addition, the method can involve an additional step after the direct mucoadministration. This additional step can be the prophylactic mucoadministration of a prophylactic formulation to the mammal in an amount, at a frequency, and for a duration effective to prevent asthma symptoms. This prophylactic formulation also contains an antifungal agent.

In another embodiment, the invention features a method for prophylactically treating a mammal at risk for developing asthma. This method involves mucoadministering to at least a portion of the airways (e.g., nasal-paranasal airways and lung airways) of the mammal a formulation in an amount, at a frequency, and for a duration effective to prevent asthma symptoms. This formulation contains an antifungal agent.

Another embodiment of the invention features a method for treating a mammal having asthma. This method involves the steps of identifying (e.g., diagnosing) the mammal, and directly mucoadministering a formulation to at least a portion of the airways (e.g., nasal-paranasal airways and lung airways) of the mammal in an amount, at a frequency, and for a duration effective to reduce or eliminate asthma symptoms. This formulation contains an antifungal agent.

Another embodiment of the invention features a method for prophylactically treating a mammal at risk for developing asthma. This method involves the steps of identifying the mammal (e.g., diagnosing), and mucoadministering a formulation to at least a portion of the airways (e.g., nasal-paranasal airways and lung airways) of the mammal in an amount, at a frequency, and for a duration effective to prevent asthma symptoms. This formulation contains an antifungal agent.

In another aspect, the invention features a method for treating a mammal having non-invasive fungus-induced intestinal mucositis (e.g., chronic colitis and Crohn's disease). This method involves mucoadministering to the mammal a formulation in an amount, at a frequency, and for a duration effective to reduce or eliminate non-invasive fungus-induced intestinal mucositis symptoms. This formulation contains an antifungal agent and can be in the form of a regulated release capsule (e.g., pH or time regulated release capsule). The mucoadministration can be the oral application of the formulation within the digestive tract of the mammal. Alternatively, the mucoadministration can be the application of the formulation within the digestive tract of the mammal by way of an enema.

In another embodiment, the invention features a method for prophylactically treating a mammal at risk for developing non-invasive fungus-induced intestinal mucositis (e.g., chronic colitis and Crohn's disease). This method involves mucoadministering to the mammal a formulation in an amount, at a frequency, and for a duration effective to prevent non-invasive fungus-induced intestinal mucositis symptoms. This formulation contains an antifungal agent.

In another aspect, the invention features a method for treating a mammal having non-invasive fungus-induced otitis media. This method involves mucoadministering to the mammal a formulation in an amount, at a frequency, and for a duration effective to reduce or eliminate non-invasive fungus-induced otitis media. This formulation contains an antifungal agent. The mucoadministration can be the application of the formulation within the middle ear of the mammal. For example, a liquid form of the formulation can be used to irrigate the middle ear if the tympanic membrane is elevated or not intact. Alternatively, a formulation can be injected into the middle ear or a myringotomy can be used to penetrate the tympanic membrane. In addition, myringotomy tubes can be used to bypass the tympanic membrane. Further, a formulation can be mucoadministered to the middle ear through the nose and eustachian tube.

In another embodiment, the invention features a method for prophylactically treating a mammal at risk for developing non-invasive fungus-induced otitis media. This method involves mucoadministering to the mammal a formulation in an amount, at a frequency, and for a duration effective to prevent non-invasive fungus-induced otitis media. This formulation contains an antifungal agent.

In another aspect, the invention features an article of manufacture that contains packaging material (e.g., boxes, wrappings, vials, and other containers) and a formulation contained within the packaging material. This formulation contains an antifungal agent. The packaging material contains a label or package insert indicating that the formulation can be directly mucoadministered to at least a portion of the nasal-paranasal anatomy of a mammal having non-invasive fungus-induced rhinosinusitis in an amount, at a frequency, and for a duration effective to reduce or eliminate non-invasive fungus-induced rhinosinusitis.

In another embodiment, the invention features an article of manufacture that contains packaging material and a formulation contained within the packaging material. This formulation contains an antifungal agent and the packaging material contains a label or package insert indicating that the formulation can be mucoadministered to at least a portion of the nasal-paranasal anatomy of a mammal at risk for developing non-invasive fungus-induced rhinosinusitis in an amount, at a frequency, and for a duration effective to prevent non-invasive fungus-induced rhinosinusitis.

Another embodiment of the invention features an article of manufacture that contains packaging material and a formulation contained within the packaging material. This formulation contains an antifungal agent. The packaging material contains a label or package insert indicating that the formulation can be directly mucoadministered to at least a portion of the airways of a mammal having asthma in an amount, at a frequency, and for a duration effective to reduce or eliminate asthma symptoms.

Another embodiment of the invention features an article of manufacture that contains packaging material and a formulation contained within the packaging material. This formulation contains an antifungal agent and the packaging material contains a label or package insert indicating that the formulation can be mucoadministered to at least a portion of the airways of a mammal at risk for developing asthma in an amount, at a frequency, and for a duration effective to prevent asthma symptoms.

Another embodiment of the invention features an article of manufacture that contains packaging material and a formulation contained within the packaging material. This formulation contains an antifungal agent. The packaging material contains a label or package insert indicating that the formulation can be mucoadministered to a mammal having non-invasive fungus-induced intestinal mucositis in an amount, at a frequency, and for a duration effective to reduce or eliminate non-invasive fungus-induced intestinal mucositis symptoms.

Another embodiment of the invention features an article of manufacture that contains packaging material and a formulation contained within the packaging material. This formulation contains an antifungal agent and the packaging material contains a label or package insert indicating that the formulation can be mucoadministered to a mammal at risk for developing non-invasive fungus-induced intestinal mucositis in an amount, at a frequency, and for a duration effective to prevent non-invasive fungus-induced intestinal mucositis symptoms.

Another embodiment of the invention features an article of manufacture that contains packaging material and a formulation contained within the packaging material. This formulation contains an antifungal agent. The packaging material contains a label or package insert indicating that the formulation can be mucoadministered to a mammal having non-invasive fungus-induced otitis media in an amount, at a frequency, and for a duration effective to reduce or eliminate non-invasive fungus-induced otitis media symptoms.

Another embodiment of the invention features an article of manufacture that contains packaging material and a formulation contained within the packaging material. This formulation contains an antifungal agent and the packaging material contains a label or package insert indicating that the formulation can be mucoadministered to a mammal at risk for developing non-invasive fungus-induced otitis media in an amount, at a frequency, and for a duration effective to prevent non-invasive fungus-induced otitis media symptoms.

In another aspect, the invention features the use of an antifungal agent for the manufacture of a medicament for the treatment or prevention of non-invasive fungus-induced rhinosinusitis.

In another embodiment, the invention features the use of an antifungal agent for the manufacture of a medicament for the treatment or prevention of asthma symptoms.

Another embodiment of the invention features the use of an antifungal agent for the manufacture of a medicament for the treatment or prevention of non-invasive fungus-induced intestinal mucositis.

Another embodiment of the invention features the use of an antifungal agent for the manufacture of a medicament for the treatment or prevention of non-invasive fungus-induced otitis media.

In another aspect, the invention features an antifungal formulation containing an antifungal agent, a flavoring, and water. The water constitutes at least about 50 percent of the formulation. For example, the water can constitute at least about 55, 60, 65, 70, 75, 80, 85, 90, 95, or 99 percent of the formulation.

In another embodiment, the invention features an antifungal formulation containing itraconazole and water. The itraconazole is dissolved in the formulation at a concentration greater than about 25 µg per mL. For example, the itraconazole can be dissolved in the formulation at a concentration greater than about 30, 40, 50, 60, 70, 80, 90, 100, 110, 120, 130, 140, 150, 160, 170, or 180 µg per mL. In addition, the water constitutes at least about 50 percent of the formulation. For example, the water can constitute at least about 55, 60, 65, 70, 75, 80, 85, 90, 95, or 99 percent of the formulation. The formulation also can contain polyethylene glycol (e.g., PEG-200, PEG-400, PEG-800, etc.). The formulation also can contain flavoring (e.g., peppermint oil, cherry flavoring, syrup, and the like).

In another embodiment, the invention features an antifungal formulation containing itraconazole and water. The itraconazole is suspended in the formulation at a concentration greater than about 25 μg per mL. For example, the itraconazole can be suspended in the formulation at a concentration greater than about 30, 40, 50, 60, 70, 80, 90, 100, 110, 120, 130, 140, 150, 160, 170, or 180 μg per mL. In addition, the water constitutes at least about 50 percent of the formulation. For example, the water can constitute at least about 55, 60, 65, 70, 75, 80, 85, 90, 95, or 99 percent of the formulation. The formulation also can contain polyethylene glycol (e.g., PEG-200, PEG-400, PEG-800, etc.). The formulation also can contain flavoring (e.g., peppermint oil, cherry flavoring, syrup, and the like).

In another embodiment, the invention features an antifungal formulation containing an antifungal agent, a flavoring, and water. The water constitutes at least about 50 percent of the formulation. For example, the water can constitute at least about 55, 60, 65, 70, 75, 80, 85, 90, 95, or 99 percent of the formulation. In addition, the antifungal agent can be amphotericin B, ketoconazole, saperconazole, voriconazole, flucytosine, miconazole, fluconazole, griseofulvin, clotrimazole, econazole, terconazole, butoconazole, oxiconazole, sulconazole, ciclopirox olamine, haloprogin, tolnaftate, naftifine, terbinafine hydrochloride, morpholines, nystatin, natamycin, butenafine, undecylenic acid, Whitefield's ointment, propionic acid, and caprylic acid.

In another aspect, the invention features a method of making an antifungal formulation. The formulation contains itraconazole and water. The itraconazole is dissolved in the formulation at a concentration greater than about 25 μg per mL. For example, the itraconazole can be dissolved in the formulation at a concentration greater than about 30, 40, 50, 60, 70, 80, 90, 100, 110, 120, 130, 140, 150, 160, 170, or 180 μg per mL. The water constitutes at least 50 percent of the formulation. For example, the water can constitute at least about 55, 60, 65, 70, 75, 80, 85, 90, 95, or 99 percent of the formulation. The method includes adding the water to a stock solution containing the itraconazole.

In another aspect, the invention features a method for culturing fungus from a mammal's mucus. The method includes (1) contacting the mucus with a mucolytic agent to reduce the viscosity of the mucus, (2) separating the fungus from the reduced-viscosity mucus, (3) contacting the separated fungus with fungus growth medium to form a fungus culture, and (4) incubating the fungus culture such that the separated fungus grows.

In another aspect, the invention features a method for obtaining a fungal antigen. The method includes (1) contacting a mammal's mucus with a mucolytic agent to reduce the viscosity of the mucus, (2) separating fungus from the reduced-viscosity mucus, (3) contacting the separated fungus with fungus growth medium to form a fungus culture, (4) incubating the fungus culture such that the separated fungus grows, and (5) isolating the antigen from the cultured fungus.

In another aspect, the invention features a method for producing a fungus-specific antibody. The method includes (1) contacting a mammal's mucus with a mucolytic agent to reduce the viscosity of the mucus, (2) separating fungus from the reduced-viscosity mucus, (3) contacting the separated fungus with fungus growth medium to form a fungus culture, (4) incubating the fungus culture such that the separated fungus grows, (5) isolating a fungal antigen from the cultured fungus, and (6) immunizing an animal with the fungal antigen to produce the antibody.

In another aspect, the invention features a nasal mucus collecting apparatus. The apparatus contains a collection retainer, a collection tube, and a connecting portion. The collection retainer is suitable for retaining mucus. The collection tube extends from the collection retainer and defines a distal end and a lumen such that mucus can traverse the lumen from the distal end of the collection tube to the collection retainer. The collection tube is generally flexible over at least a portion of the tube's length such that the collection tube can be selectively manipulated into a desired configuration by a practitioner during a collection procedure. The collection tube further is generally malleable such that the collection tube generally retains the desired configuration until the practitioner manipulates the collection tube to conform to a different configuration. The connecting portion extends from the collection retainer and defines a second lumen that communicates with the interior of the collection retainer. The connecting portion is adapted to receive a vacuum source. In addition, the apparatus can further contain a valve that adjusts the opening of the second lumen. The collection retainer can be removable from the collection tube and the connection portion.

In another aspect, the invention features a pharmaceutical composition containing an antifungal agent.

In another embodiment, the invention features a pharmaceutical composition containing an antifungal agent and an mucolytic agent.

Another embodiment features a pharmaceutical composition containing an antifungal agent and a steroid.

Another embodiment features a pharmaceutical composition containing an antifungal agent and a decongestant.

Another embodiment features a pharmaceutical composition containing an antifungal agent and an antibiotic.

Another embodiment features a pharmaceutical composition containing an antifungal agent and an anti-inflammatory.

Another embodiment features a pharmaceutical composition containing an antifungal agent and an anti-histamine.

Another embodiment features a pharmaceutical composition containing an antifungal agent and an anti-cholinergic.

Another embodiment features a pharmaceutical composition containing an antifungal agent and a leukotriene inhibitor.

In another aspect, the invention features a composition for treating an immune response to fungus in a mammal, characterized by an agent configured for direct mucoadministration to the mucus of the mammal and having antifungal means for eliminating or reducing the fungus below a threshold level wherein the fungus ceases to activate eosinophile migration to the affected area.

In another aspect, the invention features a pharmaceutical composition for treating a fungal related condition in the nasal-sinus anatomy, pulmonary anatomy, ear anatomy, or intestinal anatomy of a mammalian patient, said composition comprising an effective dose of an anti-fungal as described herein.

In another aspect, the invention features a pharmaceutical composition for treating a fungal related condition in the nasal-sinus anatomy, pulmonary anatomy, ear anatomy, or intestinal anatomy of a mammalian patient, said composition comprising an effective dose of an anti-fungal and at least one other agent or inhibitor as described herein.

In another aspect, the invention features a pharmaceutical composition for treating a fungal related condition in the nasal sinus anatomy, pulmonary anatomy, ear anatomy, or intestinal anatomy of a mammalian patient, said composition comprising an effective dose of an anti-fungal suitable for long term use within the nasal-sinus anatomy.

In another aspect, the invention features a medication for treating sinusitis, asthma, otitis media, or colitis of a patient, comprising a mucolytic agent; and an anti-fungal compound as described herein.

In another aspect, the invention features an irrigation medication for treating an inflamed nasal area, lung area, ear area, or intestinal area of a patient, the inflamed nasal area, lung area, ear area, or intestinal area being caused by the presence of a fungus, the medication comprising effective doses of an antifungal compound and a steroid as described herein.

In another aspect, the invention features an irrigation medication for treating an inflamed nasal area, lung area, ear area, or intestinal area of a patient, the inflamed nasal area, lung area, ear area, or intestinal area being caused by the presence of a fungus, the medication comprising effective doses of an antifungal compound and a mucolytic agent.

In another aspect, the invention features an irrigation medication for treating an inflamed nasal area, lung area, ear area, or intestinal area of a patient, the inflamed nasal area, lung area, ear area, or intestinal area being caused by the presence of a fungus, the medication comprising effective doses of a steroid and a mucolytic agent as described herein.

In another aspect, the invention features an irrigation medication for treating an inflamed nasal area, lung area, ear area, or intestinal area of a patient, the inflamed nasal area, lung area, ear area, or intestinal area being caused by the presence of a fungus, the medication comprising effective doses of an antifungal compound, a steroid, and a mucolytic agent as described herein.

In another aspect, the invention features an irrigation medication for treating an inflamed nasal area, lung area, ear area, or intestinal area of a patient, the inflamed nasal area, lung area, ear area, or intestinal area being caused by the presence of a fungus, the medication comprising an effective dose of at least one medicine selected from the group consisting of an antifungal compound, a steroid, a mucolytic agent, and any combination thereof as described herein.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DETAILED DESCRIPTION

Figure 1:
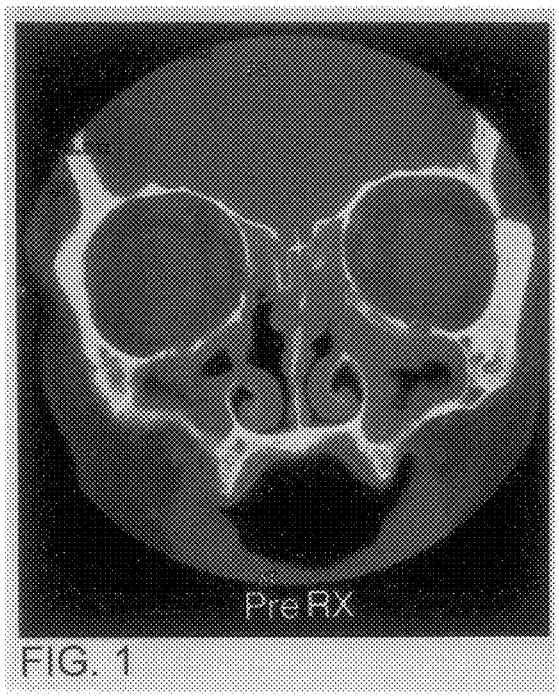
FIG. 1 is a CT scan of a patient with bilateral chronic rhinosinusitis.

The invention involves methods and materials for treating and preventing non-invasive fungus-induced mucositis. Specifically, the invention involves mucoadministering an antifungal agent in an amount, at a frequency, and for a duration effective to prevent, reduce, or eliminate chronic non-invasive fungus-induced rhinosinusitis. This invention also provides methods and materials for diagnosing chronic non-invasive fungus-induced rhinosinusitis and culturing non-invasive fungus from a mammalian mucus sample as well as specific antifungal formulations and medical devices for treating and preventing non-invasive fungus-induced rhinosinusitis. In addition, the invention provides methods and materials for treating and preventing other non-invasive fungus-induced mucositis conditions such as chronic otitis media, chronic colitis, and Crohn's disease. Further, the invention involves methods and materials for treating and preventing chronic asthma symptoms.

Although not limited to any particular mode of action, the present invention involving the treatment and prevention of non-invasive fungus-induced inflammation of mucosal tissue by using an antifungal agent is based on the following proposed mechanism of disease progression derived from the discoveries reported herein. In general, most, if not all, individuals have fungal organisms living in their mucus. Normally, most individuals tolerate these non-invasive organisms and live normal disease-free lives. For unknown reasons, some individuals do not tolerate these fungal organisms and begin to mount an immune response against them. As the immune response progresses, eosinophils accumulate within the local tissue. This accumulation of eosinophils can contribute to the formation of obstructive tissue masses (e.g, polyps and polypoid structures) as well as the transmigration of activated eosinophils from the tissue (inside the body) to the mucus (outside the body). These obstructive tissue masses appear to prevent normal cavity clearance and thus can facilitate additional fungal growth. Once eosinophils are within the mucus, they can release the contents of their granules presumably upon the activation of surface Fc receptors. Eosinophil granules contain many toxic molecules such as eosinophil cationic protein (ECP), eosinophil peroxidase (EPO), and major basic protein (MBP). Upon release, these toxic molecules can damage both the targeted foreign microorganisms (e.g., fungus) as well as self tissues. The degree of damage caused by eosinophil accumulation and eosinophil degranulation varies significantly from slight inflammatory pain and discomfort to major structural abnormalities such as tissue and bone destruction and the formation of polyps, polypoid structures, and other tumors. Once self tissues are damaged, the individual can have an increased susceptibility to bacterial infections as well. Thus, the characteristic inflammatory responses, resulting damages, and resulting bacterial infections observed within most, if not all, chronic rhinosinusitis patients are actually triggered by non-invasive fungal organisms.

It is noted that fungal organisms may be observed within the tissue under extreme mucositis conditions of tissue and bone destruction simply because the barrier (i.e., epithelium) between the inside and outside of the body has been destroyed or damaged. In these situations, the mere observed presence of a small number of fungal organisms within a localized area of tissue damage does not deter from the fact that the affliction is a non-invasive fungus-induced mucositis and not an infection.

The discovery that most, if not all, chronic rhinosinusitis cases are caused by non-invasive fungal organisms suggests that other chronic inflammatory conditions such as chronic otitis media, chronic colitis, and Crohn's disease are most likely caused by non-invasive fungal organisms living within mucus. In addition, the discovery that non-invasive fungus-induced rhinosinusitis can be successfully treated and prevented with antifungal agents when mucoadministered in an effective amount, at an effective frequency, and for an effective duration suggests that these other non-invasive fungus-induced mucositis conditions also can be treated and prevented with antifungal agents when used appropriately as described herein. Further, the discovery that chronic asthma symptoms can be treated and prevented with antifungal agents when directly mucoadministered to the airways by way of nasal-paranasal irrigation suggests that antifungal agents can be effective when directly mucoadministered to the airways by inhalation through the nose or mouth. Thus, the methods and materials described herein have the potential to treat millions of people suffering from chronic rhinosinusitis, chronic otitis media, chronic colitis, Crohn's disease, and any other non-invasive fungus-induced mucositis condition as well as chronic asthma.

As described above, a non-invasive fungus-induced mucositis is an inflammation, not an infection. In general, inflammations are fundamentally and clinically different from infections. An infection is defined as the growth of an organism within tissue. In addition, an infection is characterized as an invasive disease meaning that an infectious organism enters the tissue of a host and then triggers a host immune response and/or causes damage. Thus, the role of the infectious organism is typically that of an invasive pathogen. In addition, an infected individual can be immunocompetent or immunocompromised. When the infected individual is immunocompromised, the infection is often termed an "opportunistic" infection. Further, infections can be acute or chronic depending upon multiple factors such as the competence of the infected individual's immune system, the nature of the invasive pathogen, and the availability of medical treatments.

In contrast, an inflammation is characterized as a localized protective response that serves to destroy, dilute, and/or sequester an injurious agent or insult. In addition, inflammatory responses typically result in redness, swelling, heat, and pain. In the case of non-invasive fungus-induced mucositis, the localized protective response is against a non-invasive fungal organism living outside the tissue (e.g., within mucus). Typically, some individuals suffering from a non-invasive fungus-induced mucositis are atopic and/or immunocompetent. In addition, the role of the injurious agent (i.e., fungus) is that of a non-invasive allergen. Thus, a non-invasive fungus-induced mucositis is an allergic reaction mounted by the individual's immune system against a fungal organism living outside an individual's tissue.

As described herein, the invention provides methods and materials that reduce the presence of fungal organisms within mucus to a level and for a period of time such that the characteristic inflammatory responses and resulting damages associated with mucositis are stopped, treated, or prevented. For the purpose of clarity, reducing the presence of fungal organisms within mucus to treat or prevent mucositis is similar to removing an allergen (e.g., pollen) from the presence of an individual suffering from an allergic reaction (e.g., hay fever). Again, the allergic reaction against, for example, pollen is not an infection but an inflammation. In addition, the simplicity of this invention underscores the far-reaching clinical implications that follow these discoveries. For example, once clinicians understand that most, if not all, chronic rhinosinusitis is caused by non-invasive fungal organisms and that this inflammatory disease can be treated and prevented by reducing the level of non-invasive fungal organisms within nasal-paranasal mucus using the methods and materials described herein, then millions of people will be able to have healthier, happier, and more productive lives.

Identifying Non-Invasive Fungus-Induced Mucositis

A non-invasive fungus-induced mucositis is defined as an inflammation of any mucosal tissue induced by a non-invasive fungal organism. Examples of mucosal tissue include, without limitation, the mucosa of the mouth, gut, nasal passages, paranasal sinuses, airways of the lung, trachea, middle ear, eustachian tube, vagina, and urethra. In general, an inflammation of a mucosal tissue can be determined using any of the methods commonly known to a skilled artisan. For example, an individual can be identified as having an inflammation of a mucosal tissue upon examination of a tissue biopsy as well as by visual examination, endoscopic analysis, and image analysis techniques (e.g., X-rays, CT scans, and magnetic resonance imagery (MRI) scans) since the various inflamed mucosal anatomies tend to exhibit observable abnormal characteristics.

Multiple diagnostic methods can be used to determine if a particular mucositis is a non-invasive fungus-induced mucositis. In general, such diagnostic methods include, without limitation, reviewing the affected individual's prior medical conditions and treatments, interviewing and evaluating the affected individual, and collecting and analyzing biological samples from the affected individual.

Reviewing an affected individual's medical history can be helpful in determining if a particular mucositis is a non-invasive fungus-induced mucositis since such inflammations are typically recurrent and chronic. Thus, signs of a previous non-invasive fungus-induced mucositis episode would suggest that an instant mucositis is a non-invasive fungus-induced mucositis as well. Other useful information within an individual's medical history could include, without limitation, allergies, surgeries, and other diseases such as cystic fibrosis and ciliary dismotility syndromes.

Interviewing and evaluating an affected individual can also help identify a non-invasive fungus-induced mucositis. For example, individuals suffering from chronic mucositis symptoms such as airway obstructions, loss of smell, loss of hearing, wheezing, dyspnea, coughing, head ache, and facial pressure may have a non-invasive fungus-induced mucositis. In addition, a non-invasive fungus-induced mucositis can be ruled out in individuals that exhibit the symptoms of an infection such as fever, fungal dissemination, fungemia, increase in polymorphonuclear leukocytes, and acute onset. It is noted that recurrent bacterial infections can indicate an underlying non-invasive fungus-induced mucositis condition since chronic inflammation can lead to the destruction of the epithelium and thus increase the individual's susceptibility to bacterial infection. Further, multiple diagnostic tests can be performed to help identify a non-invasive fungus-induced mucositis. For example, a common allergy screen using a panel of fungal and non-fungal antigens can be used to determine if an individual is atopic since some cases of non-invasive fungus-induced mucositis involve atopic individuals. Further, immuno-based tests for the presence of anti-fungal antigen antibodies, tests for abnormal pulmonary function with or without methacholine, audiograms, and tympanograms can be used to identify a non-invasive fungus-induced mucositis.

Collecting and analyzing biological samples from an affected individual can help identify a non-invasive fungus-induced mucositis. In general, biological samples such as mucus, stool, urine, sputum, and blood can be collected and analyzed for signs that indicate the involvement of a non-invasive fungal organism. Such signs can include, without limitation, the presence of any antigenic marker for non-invasive fungus-induced mucositis; the presence of eosinophils, eosinophil products (e.g., MBP and ECP), antibodies, fungal antigens, or fungal organisms within a mucus, stool, urine, or sputum sample; and the absence of fungal organisms within a blood sample. For example, the identification of allergic mucus (i.e., mucus that contains evidence of eosinophil presence) can indicate a non-invasive fungus-induced mucositis. Such evidence of eosinophil presence includes, without limitation, the presence of intact eosinophils, necrotic eosinophils, and eosinophil products. Many methods for detecting the presence of these various signs and markers within a biological sample are well known in the art and can be used. For example, the presence of eosinophils within allergic mucus can be determined using a hematoxylin/eosin stain followed by microscopic examination.

In addition, a tissue biopsy can be collected and analyzed for the lack of invasive fungus. As noted above, fungal organisms may be observed within tissue under extreme mucositis conditions of tissue and bone destruction when examining a tissue biopsy simply because the barrier (i.e., epithelium) between the inside and outside of the body has been destroyed or damaged. In these situations, the mere presence of a small amount of fungal organisms within a localized area of tissue damage does not necessarily mean the affliction is not a non-invasive fungus-induced mucositis.

Further, immuno-based assays can be used to detect the presence of various signs of a non-invasive fungus-induced mucositis within a biological sample. Many immuno-based assays are well known in the art including, without limitation, enzyme-linked immunosorbent assays (ELISA) and radioallergosorbant tests (RAST). The methods of using RAST are described, for example, in McRury J et al. (*Clin Exp Immunol* 65:631–638 (1986)), Mabry R L and Manning S (*Otolaryngol Head Neck Surg.* 113:721–723 (1995), and Lynch N R et al. (*Int Arch Allergy Immunol* 114:59–67 (1997)). Immuno-based assays can use polyclonal antibodies, monoclonal antibodies, or fragments thereof that have specificity for an antigen that can be used as a diagnostic marker for non-invasive fungus-induced mucositis. For example, monoclonal antibodies having specificity for fungal organisms known to cause non-invasive fungus-induced mucositis can be produced and used to screen biological samples. Such antibodies can be produced using methods described elsewhere (Zeidan et al., Experimental Approaches in Biochemistry and Molecular Biology, William C. Brown Publisher (1996) and Seaver, Commercial Production of Monoclonal Antibodies: A Guide for Scale-Up, Marcel Dekker Inc., New York, N.Y. (1987)). Briefly, a mouse can be immunized with a sample of a fungal organism isolate. Several weeks later lymphocytes from spleen of the immunized mouse can be recovered and fused with myeloma cells to produce hybridoma cells. Hybridoma cells exhibiting specificity for the immunizing fungal isolate then can be isolated and monoclonal antibody preparations produced.

Since the specific methods and materials used to identify non-invasive fungus-induced mucositis can vary depending upon the specific location of the mucositis, a more detailed description is provided below for several exemplary mucosal tissues.

1. Nasal-Paranasal Cavities

The external bony framework of the nose consists of two oblong nasal bones. One nasal bone is disposed on each side of a midline, with the two bones forming an arched cross section. The nasal septum divides the nasal cavity in half. The lateral nasal wall has three turbinates that increase the mucosal surface area of the nasal cavity or vestibule. The nasal vestibule is bounded by the nasal septum and lateral wall. This large surface area of the turbinates and nasal septum promotes extensive contact with inspired air, thus facilitating humidification, particle removal, and temperature regulation of inspired air.

The paranasal sinuses are air-containing spaces joining the nasal cavity by means of openings or ostia. Although they are paired, the paranasal sinuses are commonly asymmetrical in shape and location, and include the maxillary, frontal, ethmoid, and sphenoid sinuses. Suggested functions of the paranasal sinuses include lightening the bones of the skull, providing mucus for the nasal cavity, and acting as resonant chambers for the production of sound. The maxillary sinuses are the largest of the paranasal sinuses. Each maxillary sinus is located in the maxilla and opens into the middle meatus. The frontal sinuses are located in the frontal bone and are superior and medial to the orbit of the eye. The frontal sinuses also empty into the middle meatus. The ethmoid sinuses are numerous and irregularly shaped air spaces opening into the middle and superior meatuses. The sphenoid sinus is in the sphenoid bone and is posterior to both the eye and the upper portion of the nasal cavity. The sphenoid sinus drains into the superior meatus.

Mucosal tissue (mucosa) lines both the nasal cavity and the paranasal sinuses, and generally comprises an epithelial layer, connective tissue, and mucus glands. A layer of mucus normally covers the mucosa. Mucus that is secreted from mucosa serves to trap particles and to prevent dehydration of the nasal and paranasal tissues that are otherwise exposed to air. The mucus is normally transported by cilia toward the nasopharynx and then swallowed.

Individuals suffering from rhinosinusitis can be identified using methods commonly known in the art. Symptoms of rhinosinusitis include, without limitation, nasal airway obstruction, loss of smell, facial pain, head ache, post nasal drip, and rhinorrhea. Upon examination, the presence of thick mucus or the visual identification of nasal or paranasal obstruction with mucus or polyps often indicates a rhinosinusitis condition. Nasal polyps are outgrowths from the nasal-paranasal mucosa that are typically smooth, gelatinous, semitranslucent, round or pear shaped, and pale. In general, nasal polyps are located on the lateral wall of the nose, usually in the middle meatus or along the middle and superior turbinates. Most nasal polyps arise from the ethmoid sinus but some polyps originate in the maxillary sphenoid sinuses. The mass of a nasal polyp is composed mainly of edematous fluid with sparse fibrous cells and a few mucous glands. The surface epithelium of nasal and paranasal polyps generally reveals squamous metaplasia. Eosinophils are usually present in polyps in moderate to large numbers, and it is now known that nasal polyp fluid contains greater than normal concentrations of IgA, IgE, IgG, and IgM antibodies as well as abnormally high concentrations of IL-5, a cytokine that contributes to eosinophil activation and survival. As demonstrated herein, the presence of nasal polyps is not a risk factor for rhinosinusitis, but rather an end stage of chronic inflammation.

The following methods and materials can be used to identify individuals suffering from non-invasive fungus-induced rhinosinusitis. As described above, the condition known as AFS is a non-invasive fungus-induced rhinosinusitis condition. Thus, any method known in the art that is used to identify AFS can be used to identify non-invasive fungus-induced rhinosinusitis (Cody D T et al. *Laryngoscope* 104:1074–1079 (1994) and Kupferberg S B et al., *Otolaryngol. Head Neck Surg* 117:35–41 (1997)). For example, non-invasive fungus-induced rhinosinusitis can be identified by the presence of inspissated mucus that contains clumps or sheets of necrotic eosinophils, Charcot-Leyden crystals, and non-invasive fungal hyphae. In addition, image analysis such as MRI and CT scans can be used to identify non-invasive fungus-induced rhinosinusitis since such conditions typically exhibit a characteristic appearance and often cause bone erosion in adjacent structures (Quraishi et al., *Otolaryngol. Head Neck Surg.* 117:29–34 (1997); Manning et al., *Laryngoscope* 107:170–176 (1997); Kinsella et al., *Head & Neck* 18:211–217 (1996); Allbery et al., *RadioGraphics* 15:1311–1327 (1995); Roth M R, *Ear, Nose & Throat J.* 73:928–930 (1994); and Bartynski et al., *Otolaryngol. Head Neck Surg.* 103:32–39 (1990)). Further, individuals with non-invasive fungus-induced rhinosinusitis may have a history of nasal-paranasal polyposis and may have undergone multiple surgeries.

Results using currently available diagnostic methodology indicate that about three to eight percent of chronic rhinosinusitis cases requiring surgery are AFS cases. In general, these current AFS diagnostic methods involve criteria such as the presence of a characteristic appearance on a CT scan, the presence of allergic mucus, and the presence of fungal organisms within mucus samples as confirmed by either histology or fungal growth in culture. The present invention demonstrates that greater than about 90 percent of all chronic rhinosinusitis cases have a fungal etiology based on a better understanding of chronic rhinosinusitis, improved diagnostic procedures, and the impressive success rate of the antifungal treatment approaches described herein. In addition, the present invention demonstrates that the ability to grow fungal organisms from a mucus sample is not a useful criterion for diagnosing a non-invasive fungus-induced rhinosinusitis condition, such as AFS, since most, if not all, humans have fungal organisms within their nasal-paranasal mucus (See Example 1). It is noted, however, that collecting, analyzing, and/or culturing fungal organisms from a nasal-paranasal mucus sample can provide useful diagnostic information. Such information can include, without limitation, information about the level of fungal organisms and the number of different fungal species present within a particular mucus sample.

Lack of appreciation for the non-invasive fungal etiology of chronic rhinusitis conditions appears to have occurred for several reasons. First, reliance on inadequate mucus collecting and fungus culturing techniques seems to have led to the misinterpretation of negative fungal growth results. As shown herein, these negative results were most likely false-negative results since fungal organisms can be grown from nasal-paranasal mucus samples collected from most, if not all, humans. Consequently, the ability to grow fungal organisms from a nasal-paranasal mucus sample is essentially meaningless as a diagnostic criterion for non-invasive fungus-induced rhinosinusitis conditions including AFS. Second, clinicians, during surgery, routinely wash away or discard mucus from the nasal-paranasal cavities prior to removing and examining a polyp for the presence of allergic mucus. Thus, the failure to detect allergic mucus most likely resulted from a failure to collect the proper medium in which to examine. This in turn may have led to the widely recognized and medically accepted theory that polyposis is the cause of certain inflammatory conditions in the nasal-paranasal anatomies. As discussed above, polyposis can be considered an end-stage result of chronic inflammation. Third, chronic inflammatory conditions, as described herein, can lead to recurrent bacterial infections that may have masked an underlying non-invasive fungus-induced rhinosinusitis condition. In addition, any temporary relief observed after antibacterial treatment may have complicated the diagnosis of a condition having a non-invasive fungal etiology.

Regardless, the present invention teaches that special care should be taken to preserve the mucus for analysis and that the presence of allergic mucus can be used to identify non-invasive fungus-induced rhinosinusitis. In addition, recurrent bacterial infections within the nasal-paranasal anatomy can indicate non-invasive fungus-induced rhinosinusitis.

Any individual that had a previous episode of rhinosinusitis is at risk for developing non-invasive fungus-induced rhinosinusitis. In addition, elderly individuals as well as individuals having cystic fibrosis, asthma, and a family history of nasal problems or allergies can be at risk for developing non-invasive fungus-induced rhinosinusitis. Further, individuals that are exposed to significant levels of allergens (e.g., fungus spores, pollen, and chemicals) can be at risk for developing non-invasive fungus-induced rhinosinusitis.

2. Middle Ear

The ear can be divided into three parts: the external ear, middle ear, and internal ear. The middle ear is a cavity that is connected to the nasopharynx by the eustachian tube. In addition, the middle ear is separated from the opening of the external ear by the tympanic membrane and contains a chain of three small bones that connect the tympanic membrane with the internal ear. Mucosal tissue lines most of the middle ear space.

Individuals suffering from an inflammation of the mucosal tissue of the middle ear (otitis media) can be identified based on a medical history of middle ear afflictions, visual examination, tissue biopsy, and symptoms such as a loss of hearing, otorrhea, and middle ear effusion.

In general, a non-invasive fungus-induced otitis media condition can be identified by (1) collecting and analyzing fluid or mucus samples from the middle ear for fungal organisms or eosinophil presence, (2) tissue biopsy analysis for non-invasive fungal organisms, (3) an audiogram consistent with conductive hearing loss, and (4) a flat tympanogram. Unlike nasal-paranasal mucus, identifying the presence of fungal organisms in samples collected from the middle ear can indicate a non-invasive fungus-induced inflammatory condition since the middle ear normally is quite sterile.

Any individual that had a previous episode of otitis media is at risk for developing non-invasive fungus-induced otitis media. In addition, young individuals (e.g., infants and toddlers) as well as individuals having a family history of ear problems or allergies can be at risk for developing non-invasive fungus-induced otitis media.

3. Intestines

Mucosal tissue lines both the small and large intestines. Individuals suffering from an inflammation of the intestines (e.g., ulcerative colitis and Crohn's disease) can be identified using methods and materials commonly known in the art. For example, tissue biopsy analysis as well as endoscopic analysis can be used to identify intestinal mucositis conditions such as intestinal polyposis. In addition, symptoms such as diarrhea, abdominal cramps, gas, and nausea can indicate inflammation of the intestines.

In general, a non-invasive fungus-induced intestinal mucositis condition can be identified by the presence of fungal organisms, eosinophils, or eosinophil products within stool samples. In addition, tissue biopsies revealing the presence of non-invasive fungal organisms can indicate a non-invasive fungus-induced intestinal mucositis condition.

Any individual that had a previous episode of an intestinal inflammatory condition is at risk for developing non-invasive fungus-induced intestinal mucositis. In addition, elderly individuals as well as individuals having a family history of digestive problems, intestinal polyposis, or allergies can be at risk for developing non-invasive fungus-induced intestinal mucositis.

Fungal Organisms

Any fungal organism living in the mucus of a mammal can be a non-invasive fungal organism that is capable of inducing mucositis since it is the mere presence of the organism in an intolerant individual's mucus that causes inflammation. For example, all fungal organisms previously identified in mucus samples of AFS patients can be non-invasive fungal organisms capable of inducing non-invasive fungus-induced mucositis including, without limitation, Absidia, *Aspergillus flavus*, *Aspergillus fumigatus*, *Aspergillus glaucus*, *Aspergillus nidulans*, *Aspergillus versicolor*, Alternaria, Basidiobolus, Bipolaris, *Candida albicans*, *Candida lypolytica*, *Candida parapsilosis*, Cladosporium, Conidiobolus, Cunninahamella, Curvularia, Dreschlera, Exserohilum, Fusarium, Malbranchia, Paecilomvces, Penicillium, Pseudalleschria, Rhizopus, Schizophylum, and Sporothrix. In addition, fungal organisms that were, until now, not identified in mucus samples of patients diagnosed positive for AFS can be non-invasive fungal organisms capable of causing a non-invasive fungus-induced mucositis including, without limitation, Acremonium, *Arachniotus citrinus*, Aurobasidioum, Beauveria, Chaetomium, Chryosporium, Epicoccum, *Exophilia jeanselmei*, Geotrichum, Oidiodendron, Phoma, Pithomyces, Rhinocladiella, Rhodoturula, Sagrahamala, Scolebasidium, Scopulariopsis, Ustilago, Trichoderma, and Zygomycete. A list of additional fungal organisms that can be non-invasive fungal organisms capable of inducing a non-invasive fungus-induced mucositis can be found in most taxonomic mycology text books.

Collecting Mucus Samples

In general, mucus can be collected from the surface of any mucosal tissue by using a collection solution to flush the mucus-containing cavity. Proper mucus collection techniques should maximize recovery of a mucus-containing collection solution by allowing sufficient penetration of the appropriate anatomic cavities and by minimizing collection solution absorption by the individual. Vasoconstrictor agents can be used to maximize mucus collection and mucolytic agents can be used to dissolve obstructive mucus such that collection solution penetration is enhanced.

Thus, before collecting a mucus sample, an individual can be treated with a vasoconstrictor agent and/or a mucolytic agent such that sufficient vasoconstriction and/or mucolytic action is induced in the appropriate region. Suitable vasoconstrictor agents can include, without limitation, phenylephrine hydrochloride (NEO-SYNEPHRINE®; Sanofi Pharmaceuticals), cocaine, and epinephrine. A mucolytic agent is any agent that liquefies mucus such that it can be recovered from the patient. Suitable mucolytic agents can include, without limitation, N-acetyl-L-cysteine (MUCOSIL™; Dey Laboratories) and recombinant human DNase (PULMOZYME®; Genentech, Inc.). Any administered vasoconstrictor agent or mucolytic agent should be allowed to take effect by waiting a sufficient period of time after administration such as about two to five minutes.

The following methods and materials can be used to collect a nasal-paranasal mucus sample. First, an individual is prepared to receive a collection solution in at least one nostril or nasal-paranasal cavity by directing the individual to inhale and to lower the chin, or in some other way constrict the access of fluids out of the mouth and down the esophagus. In a vertically sitting or standing individual, these maneuvers tend to minimize the loss or ingestion of the collection solution. Other maneuvers are also possible provided this goal is achieved. Second, an injection and collection system is configured. In general, the configuration is such that a collection solution can be administered to an individual's nostril and then efficiently collected in a container. The injection system can be, without limitation, a syringe with a curved blunt needle or tube assembly. The container can be any type of container that holds liquid. In addition, the container can be, without limitation, a storage container that is suitable for use as a transporter or sealable apparatus such that the collected sample can be handled or shipped. These containers also can contain an agent such as a preservative or antibacterial agent depending upon the desired use of the mucus sample. Third, a collection solution is administered into an individual's nostril and collected. Before administration, the individual can be instructed to expel the collection solution upon sensing the fluid in its nasal-paranasal anatomy. Alternatively, the individual can be instructed to expel the collection solution simultaneously with the administration. During administration, the collection solution can be forcibly injected into at least one nostril or side of the nasal-paranasal anatomy. The volume of the collection solution can vary according to the individual and the state of the mucositis. For example, fluid volumes can be, without limitation, between about 0.1 mL to about 100 mL or more, and specifically between about 0.1 mL and about 25 mL. The collection solution can be, without limitation, a saline solution, water, and any other suitable solution appropriate for contacting mucosal tissue. In addition, the collection solution can contain other agents that may be useful for the collection of mucus such as a mucolytic agent.

One goal of a collection solution is to dislodge and remove mucus within mucus-containing cavities. In addition to a collection solution acting as a natural flushing agent, the penetrating effect of a mucolytic agent within a collection solution can help liquefy thick obstructive mucus. Further, the combination of the force of administration with the near simultaneous pressurized expulsion by an individual can help dislodge and collect mucus. Typically, a collection solution can be administered during a period of less than about 5 seconds per side. In addition, a collection solution can be administered during a period of less than about 3 seconds. Alternatively, the time period of collection solution administration can be extend beyond 5 seconds depending on specific factors such as the degree of inflammation, the presence of obstructions, and the size of the individual. In addition, a greater than 5 second administration can be used when very small volumes or streams of collection solution are desired.

Other collection procedures also can be used to collect mucus samples, particularly if an individual is unable to comply or cope with a liquid collection procedure. Such additional procedures are well known in the art and include, without limitation, the surgical removal of mucus, a swab or mechanical mucus extraction procedure, and pressure or vacuum systems that extract mucus. In addition, these other collection procedures as well as the methods and materials described herein can be modified or adapted to obtain biological fluids from other areas of the body such as the middle ear and intestines.

After a mucus sample is collected, the sample can be analyzed for the presence of markers that indicate the involvement of non-invasive fungus-induced mucositis. For example, a mucus sample can be examined to determine the presence of allergic mucus. In addition, fungal organisms can be cultured and analyzed from a mucus sample using the techniques described herein as well as those techniques known in the art.

Figure 4:
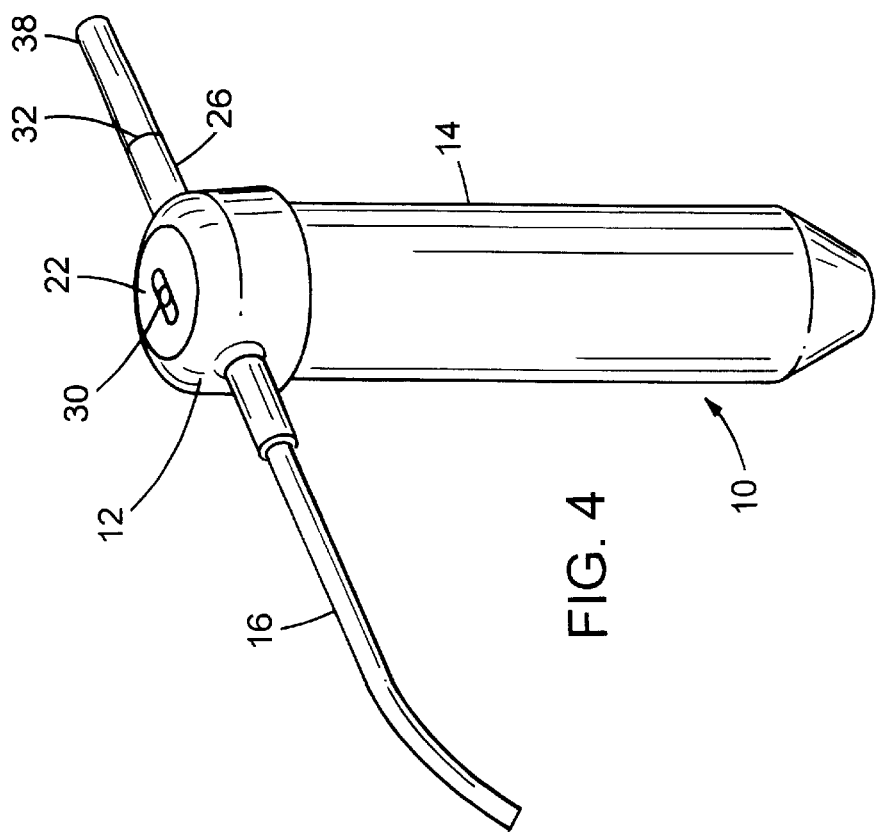
FIG. 4 is a diagram depicting a device for collecting mucus.
Figure 3:
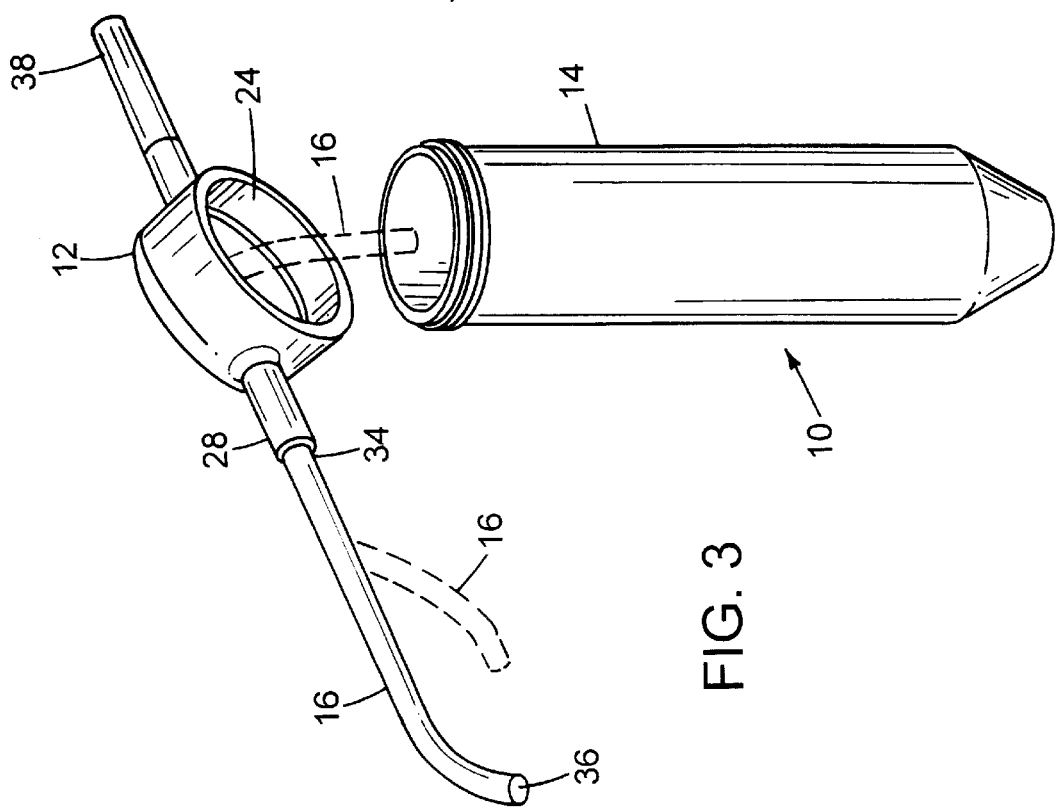
FIG. 3 is a diagram depicting a device for collecting mucus.

FIGS. 3 and 4 depict an exemplary device 10 for aspirating and collecting mucus and other liquids. Device 10 includes upper member 12, collection retainer 14, and collection tube 16. Upper member 12, in turn, broadly includes central portion 22, threaded portion 24, connecting portion 26, and tube receiving member 28. Central portion 22 may generally define opening 29 therein. Valve 30 is operably disposed within opening 29. Threaded portion 24 may extend downwardly from central portion 22. Connecting portion 26 extends radially from central portion 22, is generally circular in cross-section in this embodiment, and defines bore 32. Bore 32 communicates the exterior of device 10 with an interior portion thereof. Tube receiving member 28 extends generally radially from central portion 22. Tube receiving member 28 is disposed generally opposite connection portion 26 in this embodiment. Tube receiving member 28 defines bore 34. As with bore 32, bore 34 communicates the exterior of device 10 to the interior thereof.

In this embodiment, retainer 14 is threadably received onto threaded portion 24. Retainer 14, however, may be secured to central portion 22 by other known means. Although a conically-shaped bottom configuration is depicted, retainer 14 may assume a variety of configurations and be within the scope of this invention. Collection tube 16 extends from and is disposed within bore 34. A length of tube 16 may be disposed within the interior of retainer 14 to facilitate placement of collected material. Collection tube 16 defines lumen 36 through which the collected mucus travels. In one embodiment, tube 16 comprises a flexible memory means to facilitate adaptation to different patient anatomies. That is, tube 16 remains conformed to a desired and flexible configuration, for example, as depicted by the phantom lines in the FIG. 3. Further means to facilitate travel of the mucus through the collection tube and device 10 may include a tube or device liner having material characteristics designed to minimize adherence of the mucus thereto.

In one embodiment, device 10 is designed for a single use. Device 10 may be made from a number of materials, however, synthetic resins such as polyethylene may be used. Connecting portion 26 connects device 10 to a vacuum hose 38. Thus, connecting portion 26 may have an outer configuration such that an air tight fit to vacuum hose 38 results. Valve 30 adjusts the amount of vacuum communicated through lumen 36. By adjusting valve 30, a gradually increasing or decreasing amount of vacuum may be applied thereto. In this example, valve 30 includes a generally elongate slit which is configured with a sliding member. The sliding member may be adjusted by the user so that all, none, or a portion of the elongate slit is exposed, thereby adjusting the vacuum communicated to lumen 36. A variety of other adjustment means for regulating the vacuum, however, are within the scope of this invention. Another example includes an "IV" type of valve which utilizes a roller valve to adjustably constrict a draw or collection tube.

In contrast to other devices, tube receiving member 28 and collection tube 16 extend generally perpendicularly from a longitudinal axis of retainer 14. This enables the users to better position collection tube 16 when recovering mucus and other liquids. It is recognized that other collection containers are possible within the scope of this invention which conform comfortably to a patient's facial anatomy, and which may be readily held in place by either the patient or a health care provider. Such embodiments may rely on vacuum, gravity, or other collection mechanisms provided they afford ready access for fluids being injected into the patient while simultaneously allowing drainage or withdrawal of the fluids and mucus from the patient.

In this embodiment lumen 36 is between about 1 mm and 10 mm in diameter, and between about 5 cm and 50 cm in total length. Exemplary retainer 14 is generally between about 1" to 3" in diameter and 3" to 6" in height, although various other sizes may be useful.

Device 10 is advantageously utilized to obtain mucus or fluid samples from a patient's nasal, paranasal, or pulmonary anatomy. In obtaining mucus or fluid samples, device 10 is connected to a vacuum source and valve 30 is adjusted as desired. Tube 16 is configured to a desired position. Tube 16 is then inserted into a portion of the patient's anatomy from which mucus or fluid is to be obtained. Valve 30 is further adjusted as necessary to obtain the sample, yet assure safety to the patient. The obtained mucus or fluid is collected in retainer 14. Once collection is complete, retainer 14 may be detached from upper member 12 for storage or shipment of the obtained mucus or fluid sample.

Culturing Fungal Organisms from a Mucus Sample

A mucus sample can be prepared for fungal organism culturing by treating the sample with a mucolytic agent such as N-acetyl-L-cysteine or dithiothreitol (DTT) to enhance or facilitate further liquefaction of mucus. After adding a mucolytic agent, the mucus sample can be mixed and incubated at room temperature. This liquefaction allows fungal organisms present within mucus to be released. Once liquefied, mucus can be isolated by centrifugation or other means since mucus typically forms a layer separate from the other solutions (i.e., collection solution). Once isolated, the mucus can be mixed and an aliquot placed in contact with an appropriate fungal growth medium such as growth medium agar plates. A fungal growth medium is any medium that can support the growth of a fungal organism including, without limitation, RPMI-1649, Delbecco's modified eagles medium (DMEM), inhibitory mold agar (IMA), and Bay agar. The fungal growth medium can contain antibacterial agents (e.g., chloramphenicol and ciprofloxacin) to prevent the growth of bacteria.

Once liquefied mucus is placed in contact with an appropriate fungal growth medium, the cultures can be incubated at an optimal temperature, for example, between about 20° C. and 37° C. and, in some instances, between about 25° C. and 35° C. An optimum temperature can be assessed by placing duplicate cultures at various temperatures and comparing growth rates. Typically, cultures are incubated between about two to thirty-five days at about 30° C. Once fungal growth is observed, the fungal species can be identified using procedures well known in the art and the phenotype and genotype of each fungal isolate characterized. For example, a fungal isolate can be examined to determine any drug resistant or drug susceptibility properties.

Treating and Preventing Non-Invasive Fungus-Induced Mucositis

Antifungal agents can be mucoadministered to a mammal in an amount, at a frequency, and for a duration effective to treat or prevent non-invasive fungus-induced mucositis. An "antifungal agent" is any agent that is active against a fungal organism. For example, an antifungal agent is any agent that prevents the growth of or kills a fungal organism such as antifungal polyene macrolides, tetraene macrolides, pentaenic macrolides, fluorinated pyrimidines, imidazoles, triazoles, azoles, halogenated phenolic ethers, thiocarbamates, and allylamines. In addition, antifungal agents can be agents that interpolate fungal cell wall components or act as sterol inhibitors. Specific antifungal agents within the scope of the invention include, without limitation, amphotericin B, flucytosine, ketoconazole, miconazole, itraconazole, fluconazole, griseofulvin, clotrimazole, econazole, terconazole, butoconazole, oxiconazole, sulconazole, saperconazole, voriconazole, ciclopirox olamine, haloprogin, tolnaftate, naftifine, nystatin, natamycin, terbinafine hydrochloride, morpholines, butenafine undecylenic acid, Whitefield's ointment, propionic acid, and caprylic acid as well as those agents that can be identified as antifungal agents using methods well known in the art. It is noted that a particular patient may possess a fungal organism acting as the etiological agent that is resistant to a particular antifungal agent. In such a case, an important aspect of this invention involves treating that patient with an effective antifungal agent (e.g., an antifungal agent that prevents the growth of, or kills, the fungal organism acting as the etiological agent). Such fungal organisms acting as etiological agents can be identified using the collection and culture methods described herein.

The term "mucoadministration" as used herein refers to any type of administration that places an administered agent in contact with mucus. Thus, any intravenously administered agent that does not exit the blood stream is not considered a mucoadministered agent because the agent failed to contact mucus. In addition, the term "mucoadministration" can be subdivided into "direct" and "indirect" mucoadministration. The term "direct mucoadministration" as used herein refers to any type of administration that places an administered agent in direct contact with a targeted mucus prior to crossing epithelium. For the purpose of this invention, it is to be understood that injections of an agent into a cavity containing mucus is considered direct mucoadministration if the agent contacts mucus even though an injection means (e.g., needle, tube, or catheter) may be used to cross an epithelium. Thus, using a needle to bypass the tympanic membrane and inject an agent into the middle ear is considered a direct mucoadministration that targets middle ear mucus.

It follows that any intravenously administered agent that subsequently exits the blood stream, permeates epithelium, and contacts mucus is not considered a directly mucoadministered agent because the agent crossed epithelium prior to contacting mucus. In this case, however, the intravenously administered agent is considered an indirectly mucoadministered agent since the term "indirect mucoadministration" means any type of administration that places an administered agent in contact with a targeted mucus after crossing epithelium. Again, the use of an injection means such as a needle, tube, or catheter to deliver an agent past epithelium and into direct contact with mucus does not necessarily mean the administration is an indirect mucoadministration.

It also follows that an oral administration can be either a direct or indirect mucoadministration depending on the targeted mucus. For example, an agent can be swallowed and then traverse the esophagus, stomach, and small intestine to come in direct contact with mucus in the large intestine, without having crossed an epithelium (i.e., direct mucoadministration). At the same time, the orally administered agent could be absorbed by the gut, accumulate systemically, and permeate the nasal epithelium to come in contact with nasal mucus (i.e., indirect mucoadministration). Thus, the direct and indirect nature of mucoadministration depends upon the specific route of administration as well as the specific location of the targeted mucus. Typical routes of direct and indirect mucoadministration for various mucus locations of a mammal are described below.

An effective amount of an antifungal agent or formulation containing an antifungal agent can be any amount that reduces, prevents, or eliminates non-invasive fungus-induced mucositis upon mucoadministration in a mammal without producing significant toxicity to the mammal. Typically, an effective amount can be any amount greater than or equal to the minimum inhibitory concentration (MIC) for a fungal organism or isolate present within a particular individual's mucus that does not induce significant toxicity to the individual upon mucoadministration. Some antifungal agents may have a relatively large concentration range that is effective while others may have a relatively narrow effective concentration range. In addition, the effective amount can vary depending upon the specific fungal organism or isolate since certain organisms and isolates are more or less susceptible to particular antifungal agents. Such effective amounts can be determined for individual antifungal agents using commonly available or easily ascertainable information involving antifungal effectiveness concentrations, animal toxicity concentrations, and tissue permeability rates. For example, non-toxic antifungal agents typically can be directly or indirectly mucoadministered in any amount that exhibits antifungal activity within mucus. In addition, antifungal agents that do not permeate mucosal epithelium typically can be directly mucoadministered in any amount that exhibits antifungal activity within mucus. Using the information provided herein, such effective amounts also can be determined by routine experimentation in vitro or in vivo. For example, a patient having a non-invasive fungus-induced mucositis condition can receive direct mucoadministration of an antifungal agent in an amount close to the MIC calculated from in vitro analysis. If the patient fails to respond, then the amount can be increased by, for example, ten fold. After receiving this higher concentration, the patient can be monitored for both responsiveness to the treatment and toxicity symptoms, and adjustments made accordingly.

For amphotericin B, an effective amount can be about 0.01 ng to about 1000 mg per kg of body weight of the mammal per administration when directly mucoadministered. When used as a nasal irrigation solution, an effective amount can be a volume of about 0.01 mL to about 1 liter per nostril per administration of a solution containing about 0.01 mg of amphotericin B per liter to about 1000 mg of amphotericin B per liter. Alternatively, an effective amount can be 20 mL per nostril per administration (e.g., two to four times daily) of an irrigation solution containing about 100 mg of amphotericin B per liter of saline or water. Typically, the saline or water is sterile. The effective amount can remain constant or can be adjusted as a sliding scale or variable dose depending on the individual's response to treatment. Effective amounts for other antifungal agents can be determined by a person of ordinary skill in the art using routine experimentation in view of the multiple teachings described herein.

Typically, an effective amount of any antifungal agent directly mucoadministered (e.g., itraconazole, ketoconazole, and voriconazole) can be about 0.01 ng to about 1000 mg per kg of body weight of the mammal per administration. The MIC values for voriconazole range from about 0.003 µg/mL to about 4 µg/mL depending upon the specific fungal organism or isolate tested. For fluconazole, the MIC values range from about 0.25 µg/mL to greater than about 64 µg/mL.

To help determine effective amounts of different antifungal agents, it can be useful to refer to an effective amount equivalent based on the effective amount of a common antifungal agent. For example, the direct mucoadministration of about 20 mL per nostril per administration (e.g., twice daily) of an amphotericin B irrigation solution containing about 100 mg of amphotericin B per liter is an effective amount as demonstrated herein. The effects produced by this effective amount can be used as a reference point to compare the effects observed for other antifungal agents used at varying concentrations. Once an equivalent effect is observed, then the specific effective amount for that particular antifungal agent can be determined. In this case, that particular amount would be termed an amphotericin B effective amount equivalent.

Various factors can influence the actual effective amount used for a particular application. For example, the frequency of mucoadministration, duration of treatment, combination of other antifungal agents, site of administration, degree of inflammation, and the anatomical configuration of the treated area may require an increase or decrease in the actual effective amount mucoadministered.

The frequency of mucoadministration can be any frequency that reduces, prevents, or eliminates non-invasive fungus-induced mucositis in a mammal without producing significant toxicity to the mammal. For example, the frequency of mucoadministration can be from about four times a day to about once a month, or more specifically, from about twice a day to about once a week. In addition, the frequency of mucoadministration can remain constant or can be variable during the duration of treatment. As with the effective amount, various factors can influence the actual frequency of mucoadministration used for a particular application. For example, the effective amount, duration of treatment, combination of other antifungal agents, site of administration, degree of inflammation, and the anatomical configuration of the treated area may require an increase or decrease in mucoadministration frequency.

An effective duration for antifungal agent mucoadministration can be any duration that reduces, prevents, or eliminates non-invasive fungus-induced mucositis in a mammal without producing significant toxicity to the mammal. Thus, the effective duration can vary from several days to several weeks, months, or years. In general, the effective duration for the treatment of non-invasive fungus-induced mucositis can range in duration from several days to several months. Once the antifungal applications are stopped, however, non-invasive fungus-induced mucositis may return. Thus, the effective duration for the prevention of non-invasive fungus-induced mucositis can last in some cases for as long as the individual is alive.

For anatomies that are less susceptible to fungal organism repopulation factors (e.g., a human middle ear with an intact tympanic membrane), an effective duration can range from about 10 days to about 30 days. For less sterile environments such as the nasal-paranasal anatomy, however, an effective duration can range from about 30 days to greater than about 80 days. In the respiratory tract or digestive tract, an effective duration can be from about 10 days to greater than about 30 days, or even greater than about 90 days. Again, prophylactic treatments are typically longer in duration and can last throughout an individual's lifetime.

Multiple factors can influence the actual effective duration used for a particular treatment or prevention regimen. For example, an effective duration can vary with the frequency of antifungal agent administration, effective antifungal agent amount, combination of multiple antifungal agents, site of administration, degree of inflammation, and anatomical configuration of the treated area. Further, the specific antifungal agent used can influence the actual effective duration. For example, an effective duration for treating non-invasive fungus-induced rhinosinusitis can be about 30 days for amphotericin B and about 7 days for itraconazole.

It is noted that diagnostic algorithm methods can be devised to determine or reflect appropriate effective doses, durations, and frequencies.

Formulations Containing at Least One Antifungal Agent

A formulation containing an antifungal agent can be in any form provided the formulation can be mucoadministered to a mammal in an amount, at a frequency, and for a duration effective to prevent, reduce, or eliminate a non-invasive fungus-induced mucositis. For example, a formulation within the scope of the invention can be in the form of a solid, liquid, and/or aerosol including, without limitation, powders, crystalline substances, gels, pastes, ointments, salves, creams, solutions, suspensions, partial liquids, sprays, nebulae, mists, atomized vapors, tinctures, pills, capsules, tablets, and gelcaps. In addition, the formulation can contain a cocktail of antifungal agents. For example, a formulation within the scope of the invention can contain, without limitation, one, two, three, four, five, or more different antifungal agents. Further, formulations within the scope of the invention can contain additional ingredients including, without limitation, pharmaceutically acceptable aqueous vehicles, pharmaceutically acceptable solid vehicles, steroids, mucolytic agents, antibacterial agents, anti-inflammatory agents, immunosuppressants, dilators, vaso-constrictors, decongestants, leukotriene inhibitors, anti-cholinergics, anti-histamines, therapeutic compounds, and combinations thereof In addition, a formulation can contain any one or more compounds known to be effective for inhibiting the gag reflex of a mammal.

A pharmaceutically acceptable aqueous vehicle can be, for example, any liquid solution that is capable of dissolving an antifungal agent and is not toxic to the particular individual receiving the formulation. Examples of pharmaceutically acceptable aqueous vehicles include, without limitation, saline, water, and acetic acid. Typically, pharmaceutically acceptable aqueous vehicles are sterile. A pharmaceutically acceptable solid vehicle can be formulated such that the antifungal agent is suitable for oral administration. For example, capsules or tablets can contain an antifungal agent in enteric form. The dose supplied by each capsule or tablet can vary since an effective amount can be reached by administrating either one or multiple capsules or tablets. Any well known pharmaceutically acceptable material such as gelatin and cellulose derivatives can be used as a pharmaceutically acceptable solid vehicle. In addition, a pharmaceutically acceptable solid vehicle can be a solid carrier including, without limitation, starch, sugar, or bentonite. Further, a tablet or pill formulation of an antifungal agent can follow conventional procedures that employ solid carriers, lubricants, and the like.

Steroids can be any compound containing a hydrocyclopentanophenanthrene ring structure. Examples of steroids include, without limitation, prednisone, dexamethasone, and hydrocortisone. Mucolytic agents can be any compound that liquefies mucus. Suitable mucolytic agents can include, without limitation, N-acetyl-L-cysteine (MUCOSIL™; Dey Laboratories) and recombinant human DNase (PULMOZYME®; Genentech, Inc.). An antibacterial agent can be any compound that is active against bacteria, such as penicillin, erythromycin, neomycin, gentamicin, and clindamycin. An anti-inflammatory agent can be any compound that counteracts inflammation, such as ibuprofen and salicylic acid. An immunosuppressant can be any compound that suppresses or interferes with normal immune function, such as cyclosporine. A dilator can be any compound that causes the expansion of an orifice, such as albuterol. A vaso-constrictor can be any compound that constricts or narrows blood vessels, such as phenylephrine hydrochloride (NEO-SYNEPHRINE®; Sanofi Pharmaceuticals), cocaine, and epinephrine. A decongestant can be any compound that acts to reduce nasal-paranasal congestion or swelling, such as pseudoephedrine hydrochloride, phenylpropanolamine, and oxymetazoline. A leukotriene inhibitor can be any compound that inhibits the function or synthesis of a leukotriene, such as Azelastine®. An anti-cholinergic can be any compound that blocks parasympathetic nerve impulses, such as ipratropium bromide. An anti-histamine can be any compound that opposes the action of histamine or its release from cells (e.g., mast cells), such as terfenadine and astemizole.

A therapeutic compound can be any compound that has a therapeutic effect upon administration. For example, a therapeutic compound can be any compound that blocks or interferes with the interaction of an eosinophil with an immunoglobulin bound to a fungal antigen by targeting, for example, Fc receptor or S-type lectin factor receptor (e.g., galectin-3) interactions. Such compounds can include, without limitation, antibodies such as IgE, IgA, IgG, IgM, and IgD as well as antibody fragments such as Fab, $F(ab')_2$, FcγRI, FcγRII, FcαR, FcεRII, and FcεRI.

Mucoadministration Targeting the Nasal-Paranasal Anatomies

The mucoadministration of an agent to the nasal-paranasal anatomies can be any type of administration that places the agent in contact with nasal-paranasal mucus. Direct mucoadministration to the nasal-paranasal anatomies can include, without limitation, nasal irrigations, nasal sprays, nasal inhalations, and nasal packs with, for example, saturated gauze provided the administered agent contacts nasal-paranasal mucus prior to crossing epithelium. In addition, injections into the nasal-paranasal cavities using, for example, a needle or catheter tube is considered a direct mucoadministration provided the administered agent contacts nasal-paranasal mucus after leaving the needle or catheter tube and prior to crossing epithelium. Any device can be used to directly mucoadminister an agent to the nasal-paranasal anatomy including, without limitation, a syringe, bulb, inhaler, canister, spray can, nebulizer, and mask. For example, a 20 mL bulb can be used to irrigate the nasal-paranasal anatomy with a liquid form of a formulation containing an antifungal agent. Such a liquid form of a formulation can be stored at −20° C., 0° C., or room temperature. If stored below room temperature, the formulation typically is warmed prior to application to the nasal/paranasal cavities.

Indirect mucoadministration to the nasal-paranasal anatomies can include, without limitation, oral, intravenous, intradermal, and intraperitoneal administrations provided the administered agent contacts nasal-paranasal mucus. In addition, any device can be used to indirectly mucoadminister an agent to the nasal-paranasal anatomy including, without limitation, a syringe and regulated release capsule.

It is noted that the particular route of administration can influence the effective amount and duration of treatment with antifungal agents as well as the frequency of mucoadministration. For example, orally mucoadministered antifungal agents may require higher concentrations to deliver an effective amount to nasal-paranasal mucus than direct mucoadministration by nasal irrigations.

Mucoadministration Targeting the Lung Airways

An airway is any part of the mammalian anatomy that air traverses during respiration including the mouth, nasal passages, trachea, bronchi, and bronchial tubes. A lung airway is any air passage of the lung lined by mucosa including the bronchi and bronchial tubes. The mucoadministration of an agent to the lung airways can be any type of administration that places the agent in contact with lung airway mucus. Direct mucoadministration to the lung airways can include, without limitation, inhalations, nasal sprays, and nasal irrigations provided the administered agent contacts lung airway mucus prior to crossing epithelium. In addition, injections into lung airways using, for example, a needle or catheter tube is considered a direct mucoadministration provided the administered agent contacts lung airway mucus after leaving the needle or catheter tube and prior to crossing epithelium. Any device can be used to directly mucoadminister an agent to the lung airway including, without limitation, a syringe, bulb, inhaler, nebulizer, aerosol canister, spray can, and mask.

Indirect mucoadministration to the lung airways can include, without limitation, oral, intravenous, intradermal, and intraperitoneal administrations provided the administered agent contacts lung airway mucus after crossing epithelium. In addition, any device can be used to indirectly mucoadminister an agent to lung airways including, without limitation, a syringe and regulated release capsule.

It is noted that the particular route of administration can influence the effective amount and duration of treatment with antifungal agents as well as the frequency of mucoadministration. For example, enteric mucoadministration of an antifungal agent may require a higher concentration to deliver an effective amount to lung airway mucus than direct mucoadministration by inhalation through the mouth or nose.

It is to be understood that the direct and indirect mucoadministration to the airways including the trachea, nasal passages, and mouth can be accomplished using the methods and material described herein for the lung airways.

Mucoadministration Targeting the Middle Ear

The mucoadministration of an agent to the middle ear can be any type of administration that places the agent in contact with middle ear mucus. The direct mucoadministration to the middle ear can include, without limitation, ear drops and ear flushes provided the administered agent contacts middle ear mucus prior to crossing epithelium. For example, if the tympanic membrane is damaged or otherwise punctured, then an ear flush would be considered a direct mucoadministration provided the administered agent contacts middle ear mucus. In addition, injections into the middle ear using, for example, a needle or myringotomy tube is considered a direct mucoadministration provided the administered agent contacts middle ear mucus after leaving the needle or tube and prior to crossing epithelium. Any device can be used to directly mucoadminister an agent to the middle ear including, without limitation, a syringe and bulb.

Indirect mucoadministration to the middle ear can include, without limitation, oral, intravenous, intradermal, and intraperitoneal administrations provided the administered agent contacts middle ear mucus after crossing epithelium. In addition, any device can be used to indirectly mucoadminister an agent to the middle ear including, without limitation, a syringe and regulated release capsule.

It is noted that the particular route of administration can influence the effective amount and duration of treatment with antifungal agents as well as the frequency of mucoadministration. For example, orally mucoadministered antifungal agents may require higher concentrations to deliver an effective amount to middle ear mucus than direct mucoadministration by middle ear injection.

Mucoadministration Targeting the Intestines

The mucoadministration of an agent to the intestines can be any type of administration that places the agent in contact with intestinal mucus. The direct mucoadministration to the intestines can include, without limitation, oral and enema administrations provided the administered agent contacts intestinal mucus prior to crossing epithelium. In addition, injections into the digestive tract using, for example, a needle or catheter tube is considered a direct mucoadministration provided the administered agent contacts intestinal mucus after leaving the needle or catheter tube and prior to crossing epithelium. Any device can be used to directly mucoadminister an agent to the intestines including, without limitation, a syringe and regulated release capsule. For example, an antifungal agent can be formulated into a regulated release capsule such that the antifungal agent is released after passing, for example, the stomach (e.g., pH regulated release capsules and time regulated release capsules).

Indirect mucoadministration to the intestines can include, without limitation, intravenous, intradermal, and intraperitoneal administrations provided the administered agent contacts intestinal mucus. In addition, any device can be used to indirectly mucoadminister an agent to the intestines including, without limitation, a syringe.

It is noted that the particular route of administration can influence the effective amount and duration of treatment with antifungal agents as well as the frequency of mucoadministration. For example, intravenously mucoadministered antifungal agents may require higher concentrations to deliver an effective amount to intestinal mucus than direct mucoadministration by an enema.

Additional Treatments

Other treatments can be used in combination with a formulation containing an antifungal agent to help enhance the treatment or prevention of non-invasive fungus-induced mucositis conditions. Such additional treatments can include, without limitation, surgeries and the administration of a second formulation. Surgeries can include, without limitation, the removal of polypoid growths or other tumors, the physical opening of a cavity, and the insertion of catheter tubes and the like. A second formulation can include, without limitation, antifungal agents, mucolytic agents, antibacterial agents, anti-inflammatory agents, immunosuppressants, dilators, vaso-constrictors, decongestants, steroids, anti-cholinergics, leukotriene inhibitors, anti-histamines, therapeutic compounds, and combinations thereof. In addition, this second formulation can be administered to a mammal by any route. For example, oral, intraperitoneal, intradermal, intravenous, subcutaneous, intramuscular, topical, intranasal, and intrabronchial administration can be used to deliver a second formulation to a mammal.

Treating and Preventing Asthma

Asthma can be characterized by a paradoxical narrowing of the bronchi (lung passageways) such that breathing becomes difficult. Individuals suffering from asthma can exhibit symptoms such as wheezing, difficulty breathing (particularly exhaling air), dyspnea, and tightness in the chest. Factors that can exacerbate asthma include rapid changes in temperature or humidity, allergies, upper respiratory infections, exercise, stress, and smoking. Individuals suffering from asthma can be identified using any of the known methods in the art. In general, asthma can be, without limitation, diagnosed objectively with a pulmonary function test (increased airway resistance) with or without provoking the airway (e.g., methacholine challenge test), chest X-rays, and auscultation of the chest.

Individuals at risk for developing asthma can include, without limitation, those individuals that have had a previous episode of asthma. In addition, elderly individuals; individuals having cystic fibrosis, chronic rhinosinusitis with or without gross nasal-paranasal polyps, aspirin sensitivity, or a family history of respiratory problems or allergies; and individuals that are exposed to significant levels of allergens (e.g., fungus spores, pollen, and chemicals) or irritants can be at risk for developing asthma.

Chronic asthmatic individuals can be treated by directly mucoadministering an antifungal agent to at least a portion of the airways in an amount, at a frequency, and for a duration effective to reduce or eliminate asthma symptoms. Such direct mucoadministrations can be similar to the methods and materials described herein for the treatment and prevention of non-invasive fungus-induced rhinosinusitis since the nasal-paranasal cavities are airways. For example, nasal sprays and nasal irrigations can be used to directly mucoadminister antifungal agents to airway mucus. In addition, chronic asthmatic individuals can be treated by directly mucoadministering an antifungal agent to at least a portion of the lung airways in an amount, at a frequency, and for a duration effective to reduce or eliminate asthma symptoms. For example, aerosol or powder forms of an antifungal agent can be used for direct mucoadministration to lung airway mucus by inhalation through the mouth or nose.

Further, individuals at risk for developing chronic asthma can be prophylactically treated by mucoadministering an antifungal agent to at least a portion of the airways in an amount, at a frequency, and for a duration effective to prevent asthma symptoms. Again, such prophylactic treatments can be similar to the methods and materials described herein for the prophylactic treatment of non-invasive fungus-induced rhinosinusitis.

The invention will be further described in the following examples, which do not limit the scope of the invention described in the claims.

EXAMPLES

Example 1

Collecting and Analyzing Mucus Samples

The following methods and materials were used to collect and analyze mucus from 202 patients. Prior to collecting the mucus, each patient was directed to inhale and then lower his or her chin toward their chest to minimize or prevent the flow of a collection solution out of the nasal-paranasal passageways via the normal drainage at the back of the throat. The collection solution was either a sterile saline solution or sterile water. In addition, each patient was positioned such that the flow of the collection fluid out of the nasal passageways would be minimized or prevented. Some patients received an administration of a vasoconstrictor, such as phenylephrine hydrochloride (1–2 sprays per nostril) or cocaine (topical liquid or powder; less than four mg per kg of body weight). Some patients received a spray of about three mL of a 20% solution of N-acetyl-L-cysteine. Patients receiving both were given the vasoconstrictor first and then about two minutes later given N-acetyl-L-cysteine.

Once the patient was prepared, a collection container was placed under the nostril or nostrils from which the mucus sample was to be collected. An injection device, such as a syringe-like device having a tube assembly or blunt curved needle, was then partially placed into one of the patient's nostrils or paranasal anatomy such that the collection solution could be forced through the patient's nasal-paranasal anatomy. In some cases, about five mL to about 30 mL of a collection solution was then injected into a nostril during a time period of about 0.5 and five seconds. In most cases, about ten mL to about 20 mL of a collection solution was injected into a nostril during a time period of between about 0.5 and three seconds.

In general, each patient blew out or forcefully discharged the collection solution either simultaneously as it was being injected or upon sensing its entry into the nostril. This forceful discharging of the injected collection solution contributed significantly to loosening mucus within the patient's nasal and paranasal lumens. Again, special care was taken to reduce or prevent the loss of collection solution volume. Once expelled, the collection solution containing mucus from the patient's nostril was collected in the collection container placed under the nostril. After nasal-paranasal mucus was collected, the mucus was cultured using one of the following two methods. In the first method, one mL of a 20% solution of N-acetyl-L-cysteine was added to about ten mL of the recovered collection solution containing mucus. This mixture was then vortexed for 30 seconds and incubated for 15 minutes at room temperature. After incubation, the mixture was centrifuged in a 50 mL tube for five minutes at 4800 rpm. After separation, the supernatant was discarded and the remaining mucus vortexed for 30 seconds. A 0.5 mL aliquot of the isolated mucus was then added to each culture plate, one IMA plate containing chloramphenicol and one IMA plate containing ciprofloxacin. The plates were then incubated at 30° C. and read as a routine fungal culture. Growth of individual isolates was observed from about two days to about 35 days.

In the second method, ten mL of DTT was diluted with 90 mL of sterile distilled water. An equal volume of this freshly diluted DTT solution was added to the recovered collection solution containing mucus and the mixture vortexed for 30 seconds. This mixture was then incubated for 15 minutes at room temperature. After incubation, the mixture was centrifuged in a 50 mL tube for ten minutes at 3000×g. After separation, the supernatant was discarded and the remaining mucus vortexed for 30 seconds. A 0.5 mL aliquot of the isolated mucus was then added to each culture plate, one IMA plate containing chloramphenicol and one Bay agar plate containing ciprofloxacin. The plates were then incubated at 30° C. and read as a routine fungal culture. Growth of individual isolates were observed from about two days to about 35 days.

Once fungal growth was observed, the organisms were identified using standard mycology techniques including visual, histological, and immunological techniques. Identified fungal genera and species included many fungal organisms previously isolated from AFS patients, such as Absidia, *Aspergillus flavus, Aspergillus fumigatus, Aspergillus glaucus, Aspergillus nidulans, Aspergillus versicolor,* Alternaria, Basidiobolus, Bipolaris, *Candida albicans, Candida lypolytica, Candida parapsilosis,* Cladosporium, Conidiobolus, Cunninahamella, Curvularia, Dreschlera, Exserohilum, Fusarium, Malbranchia, Paecilomvces, Penicillium, Pseudallescheria, Rhizopus, Schizophylum, and Sporothrix. In addition, fungal organisms were identified that were not previously identified in mucus samples of patients diagnosed positive for AFS, such as Acremonium, *Arachniotus citrinus,* Aurobasidioum, Beauveria, Chaetomium, Chryosporium, Epicoccum, *Exophilia jeanselmei,* Geotrichum, Oidiodendron, Phoma, Pithomyces, Rhinocladiella, Rhodoturula, Sagrahamala, Scolebasidium, Scopulariopsis, Ustilago, Trichoderma, and Zygomycete.

To determine the optimum temperature for culturing fungal organisms that cause non-invasive fungus-induced mucositis, liquefied mucus samples collected from two patients were cultured onto IMA plates containing either chloramphenicol or ciprofloxacin. Two dishes (one containing chloramphenicol and one containing ciprofloxacin) for each sample were then incubated at 25° C., 28° C., 30° C., 32° C., 33° C., 35° C., and 37° C. Each plate was visually scored for fungal growth and development every other day over a period from about two days to about 35 days from the time of culturing. The scores for each temperature were averaged, thereby providing an estimate of the optimum temperature for spore germination and subsequent growth or development of fungal organisms. The results indicated that the optimum temperature for fungal growth varied depending upon the specific fungal species or isolate. In general, 30° C. was found to support growth for the largest number of fungal species and isolates.

The following procedure was used to determine effective antifungal agents as well as effective concentrations of antifungal agents such that the fungal organisms isolated from patients can be prevented from growing or killed.

Seventeen fungal isolates were collected from eight rhinosinusitis patients and tested for susceptibility against amphotericin B, ketoconazole, and itraconazole. Each antifungal agent was tested on these fungal isolates using the macro broth dilution technique according to the National Committee on Clinical Laboratory Standards (NCCLS) protocol. A 48 hour MIC reading was recorded and interpreted using NCCLS guidelines to rate each culture as susceptible, intermediate, or resistant to the antifungal agent at the concentrations being tested. The results from this procedure provided an estimate of the efficacy of antifungal agents against specific fungal isolates in vitro. In general, the MIC values for these antifungal agents for each isolate were found to range widely between 0.03 and 100 $\mu$g/mL (Table I).

TABLE I

Fungal organisms isolated from 64 of 66 rhinosinusitis patients studied including 17 amphotericin B, ketoconazole, and itraconazole MIC values for selected isolates from eight rhinosinusitis patients.

| Fungal Organism | Number of Species/ Isolates | Amphotericin B MIC ($\mu$g/mL) | Ketoconazole MIC ($\mu$g/mL) | Itraconazole MIC ($\mu$g/mL) |
| --- | --- | --- | --- | --- |
| Acremonium | 1 | | | |
| Alternaria | 40 | 0.2 | 1.56 | neg* |
| | | 0.8 | 3.13 | neg |
| | | >5 | 12.5 | neg |
| Arachniotus citrinus | 2 | | | |
| Aspergillus | 21 | | | |
| Aurobasidium | 2 | | | |
| Candida | 13 | 0.2 | 50 | 0.03 |
| | | 0.4 | 1.56 | neg |
| | | 0.1 | 0.39 | neg |
| | | 0.2 | >100 | neg |
| Cladosporium | 21 | 3 | 1.56 | neg |
| | | 0.4 | 0.05 | neg |
| | | 0.1 | 0.05 | 0.125 |
| Chryosporium | 1 | | | |
| Epicoccum | 6 | | | |
| Exophilium Jeanselmei | 2 | | | |

TABLE I-continued

Fungal organisms isolated from 64 of 66 rhinosinusitis patients studied including 17 amphotericin B, ketoconazole, and itraconazole MIC values for selected isolates from eight rhinosinusitis patients.

| Fungal Organism | Number of Species/ Isolates | Amphotericin B MIC (μg/mL) | Ketoconazole MIC (μg/mL) | Itraconazole MIC (μg/mL) |
|---|---|---|---|---|
| Fusarium | 18 | >5 | >100 | 37° C.** |
|  |  | 2 | 100 | 1 |
|  |  | >5 | 12.5 | >16 |
| Geotrichum | 5 | 0.1 | 0.05 | 37° C. |
| Mucor | 2 |  |  |  |
| Oididendron | 1 |  |  |  |
| Paecilomyces lilacinus | 2 |  |  |  |
| Papularia | 1 |  |  |  |
| Penicillium | 30 | 0.4 | 3.13 | 0.5 |
|  |  | 1 | 1.56 | 0.25 |
| Phoma | 1 |  |  |  |
| Pithomyces | 2 |  |  |  |
| Rhodoturula | 1 |  |  |  |
| Scolebasidium | 1 |  |  |  |
| Trichoderma | 3 | 4 | 50 | 37° C. |
| Ustilago | 2 |  |  |  |
| not identified (2 monila, 3 dermatiaceous) | 7 |  |  |  |

*neg means the organism did not grow in the test medium (PEG 400);
**37° C. means the organism did not grow at 37° C.

The following study was conducted to determine the frequency of rhinosinusitis conditions having a non-invasive fungal etiology. For this study, the following criteria were used to determine if a patient had non-invasive fungus-induced rhinosinusitis: (1) presence of observable disease within the nasal-paranasal anatomy, (2) presence of allergic mucus, and (3) presence of fungal organisms within nasal-paranasal mucus. Each patient had a CT scan using standard procedures to determine the presence of observable disease within their nasal-paranasal anatomy. To determine the presence of allergic mucus, a surgical specimen was collected from each patient and evaluated histologically. It is noted that special care was used to collect each surgical specimen to ensure that mucus samples were not washed away. To determine the presence of fungal organisms within nasal-paranasal mucus, the methods and materials for collecting and culturing fungal organisms from a patient's mucus described herein were used.

Seventy-three rhinosinusitis patients were entered into the study. The ages of these patients ranged from 13 to 73 years, averaging 50.1 years of age. Thirty-nine of the 73 patients were female and 34 were male. The number of previous surgeries relating to rhinosinusitis for each patient ranged from 0 to 25, with an average of 3.41 surgeries per patient. Seventy of the 73 patients had previously experienced a recurrence of polyposis and rhinosinusitis.

Seven patients were subsequently excluded from the study due to a lack of an acceptable mucus specimen. Of the remaining 66 patients, 66 (100%) were diagnosed as CT-scan-positive, 62 (94%) were diagnosed positive for the presence of allergic mucus, and 64 (97%) had positive fungal cultures. Taken together, 60 of 66 (91%) cases of rhinosinusitis had all three criteria. In other words, 91 percent of the 66 rhinosinusitis patients evaluated have, based on the above criteria, non-invasive fungus-induced rhinosinusitis. This 91 percent proportion represents a dramatic increase in the number of rhinosinusitis cases involving non-invasive fungal organisms. For example, numerous medical research articles report that about three to eight percent of chronic rhinosinusitis cases requiring surgery are AFS cases, a rhinosinusitis condition having a non-invasive fungal etiology. Thus, the results presented herein indicate that the involvement of non-invasive fungal organisms in rhinosinusitis conditions is much more prevalent than previously appreciated.

A total of 25 different fungal species was identified from mucus specimens from these non-invasive fungus-induced rhinosinusitis patients. Sixteen organisms never before described as present coincident with AFS were detected from the 64 mucus samples that exhibited fungal growth. The range was about one to seven fungal organisms per patient with an average of about 2.9 fungal species per patient. Sixty-three percent of the cultures included Alternaria, 47 percent included Penicillium, 33 percent included Cladosporium, 33 percent included Aspergillus, 28 percent included Fusarium, and 20 percent included Candida.

In a separate study, twelve control individuals (i.e., persons not having chronic rhinosinusitis) had mucus samples collected and analyzed as described herein. All twelve (100%) had positive fungal cultures. Specifically, a total of seven different fungal organisms were cultured with an average of about 2.25 different fungal organisms per person and a range of one to four. Fifty percent of the cultures included Cladosporium, 42 percent included Alternaria, 33 percent included Geotrichum, 33 percent included Aspergillus, 25 percent included Penicillium, 8 percent included Acremonium, and 8 percent included Candida. These results indicate that fungal organisms live the nasal-paranasal mucus of most, if not all, humans.

Example 2

Treating and Preventing Non-Invasive Fungus-Induced Rhinosinusitis

One hundred and thirty-two consecutive rhinosinusitis patients were entered into a study to evaluate the use of an antifungal agent to treat non-invasive fungus-induced rhinosinusitis. After diagnostic analysis, 125 of the 132 patients (95%) had the following criteria: (1) presence of observable disease within the nasal-paranasal anatomy as evidenced by a CT scan, (2) presence of allergic mucus as evidenced by histologic evaluation of a surgical specimen, and (3) presence of fungal organisms within nasal-paranasal mucus as evidenced by the ability to culture fungal organisms from a mucus sample. The 125 non-invasive fungus-induced rhinosinusitis patients were started on an antifungal treatment of about 20 mL of an amphotericin B solution per nostril, two to four times daily for at least three months. The concentration of the amphotericin B solution was about 100 mg per liter of saline or water. A 20 mL bulb was used by the patient to mucoadminister the amphotericin B solution into the patient's nasal-paranasal anatomy. Data were compiled for 53 of the patients who had returned for their three month follow-up analysis.

In addition to patient interviewing, CT scan analysis, visual examination, and fungal culture analysis, two types of evaluations were used to score the success of the treatment: an endoscopic evaluation and a patient symptom evaluation. These evaluations were scored as follows:

Endoscopic Evaluation

Figure 2:
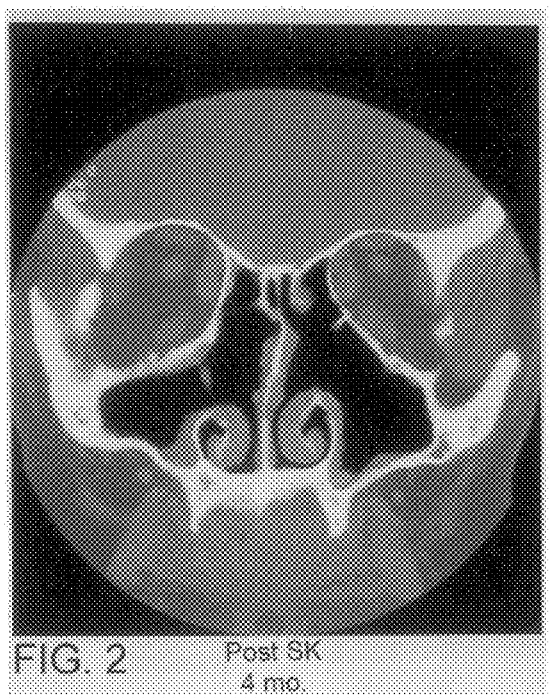
FIG. 2 is a CT scan of the patient of FIG. 1, four months later, after treatment with antifungal irrigations.

Stage 0: no evidence of disease
Stage 1: polypoid changes/polyps seen by endoscopy only Stage 2: polyps in the middle meatus
Stage 3: polyps filling the nasal cavity Patient Symptom Evaluation Stage −2: very bad/much worse
Stage −1: bad/worse
Stage 0: baseline/no change
Stage 1: good/improved
Stage 2: very good/free of symptoms Endoscopic evaluation revealed that 33 of the 53 patients went from stage 2 or 3 to stage 0 after three months. Six of these 33 cases showing no evidence of disease were confirmed by CT scans. For example, one patient having had no recent surgeries and taking no steroids was diagnosed with bilateral rhinosinusitis since a CT scan revealed bilateral involvement (FIG. 1). The patient then received the treatment of 20 mL of an amphotericin B solution (100 mg/L) per nostril two times daily. After four months of continuous antifungal treatment, a CT scan was taken to show the complete disappearance of opacity and symptoms characteristic of rhinosinusitis (FIG. 2).

Eleven of the 53 patients went from endoscopic evaluation stage 2 or 3 to stage 1 after three months. The other nine patients did not respond to the treatment. Five of the nine non-responding patients had previously collected mucus samples that were available for examination. Analysis of these five available samples revealed that all five patients had fungal organisms within their mucus that were resistant to amphotericin B, the antifungal agent used for the treatment.

Patient symptom evaluation revealed that 44 of the 53 patients gave themselves a stage 2, three of the 53 gave themselves stage 1, and six of the 53 gave themselves a stage 0 after treatment. The nine patients giving themselves a stage 1 or 0 were the same nine patients that did not have any response as measured by endoscopic evaluation, five of which were shown to contain fungal organisms resistant to amphotericin B. In a subsequent review of another patient cohort, several non-responding patients were found not to contain amphotericin B-resistant fungal organisms.

In addition, several patients had mucus samples collected and analyzed before and after antifungal treatment. Comparing results from the evaluation of mucus samples before and after antifungal treatment revealed that the number of different fungal species in those patients was remarkably reduced after antifungal treatment as determined by fungal organism culturing techniques. Thus, the rhinosinusitis patients were asymptomatic and contained less fungus in their mucus after treatment with an antifungal agent.

In a separate unique study, a patient was diagnosed with rhinosinusitis in the left paranasal sinuses since a CT scan showed inflammatory disease characteristic of rhinosinusitis-related opacification in the left paranasal sinuses. A RAST assay to Alternaria showed 6.23 kilo units per liter (KU/L) and bi-lateral fungal cultures confirmed Alternaria growth in each nostril. Only the left nasal-paranasal side, however, received surgery as well as intra-operative and post-operative treatment with about 20 mL of an amphotericin B solution (100 mg/L) two to four times daily. At every post-operative visit, the patient's left paranasal sinuses were clear of disease. A RAST reading taken eight to ten weeks after the disappearance of rhinosinusitis symptoms in the patient's left sinuses, however, was 7.16 KU/L. This represents an increase over the first RAST reading. At six months post-operation, the patient was diagnosed with rhinosinusitis in the right paranasal sinuses based on a CT scan and a 10.0 KU/L RAST reading to Alternaria. After surgery on the patient's right paranasal sinuses and antifungal treatment on both sides using about 20 mL of an amphotericin B solution (100 mg/L) per nostril two to four times daily for about seven weeks, the patient remained symptom-free and had a RAST reading of 4.47 KU/L. Six months after this last surgery, the patient remained symptom-free and disease-free as evidenced by a CT scan.

Taken together, these results indicate that an appropriate irrigation with a properly administered antifungal agent to a single side resulted in prevention of inflammatory symptoms on that side. In addition, the previously detected fungal load in the initially untreated side (right side) was sufficient to eventually cause presentation of visual or palpable rhinosinusitis symptoms in that initially untreated side. Further, the fungal organisms present in the initially untreated side (right side) induced high IgE titers, as shown by IgE readings from the RAST assays, independent of concurrent reduction of fungal organisms by antifungal treatment applied to the left side. In this case, a reduction of IgE readings from the RAST assays was only observed after irrigating both sides with an antifungal agent. Thus, the reduction of IgE and the prevention of disease symptoms coincided with the treatment of both sides with an antifungal agent.

To further evaluate the use of an antifungal agent to treat non-invasive fungus-induced rhinosinusitis, patient information was collected for each patient returning to the physician's office during a one week time period. Only previously seen patients that were instructed to use the antifungal amphotericin B nasal irrigations were entered into this study.

During a one week period, twenty patients returned to the physician's office (Table II). The average age of the returning patients was 47 years (range 16–74 years). The patients were using the amphotericin B irrigations for an average duration of about six months (range 1–16 months). Some patients had a nasal surgery as recent as one month while others never had such a surgery. In addition, some patients were using topical and systemic steroid therapy. Further, some patients were using an antibiotic nasal irrigation in addition to the antifungal irrigations. The antibacterial solution contained 80 mg gentamicin per L saline (Wilson's solution). Some patients mixed the antibacterial solution with the antifungal solution and then performed the nasal irrigations while others used each solution separately in a sequential manner. Some patients also had other diseases including asthma (15 of the 20 patients) and colitis (2 of the 20 patients).

Upon endoscopic evaluation, most patients had an observable improvement in their non-invasive fungus-induced rhinosinusitis condition. These observable improvements correlated with the symptom improvement scores given by each patient. One patient stopped the nasal amphotericin B irrigations after two months. Eight months later that patient exhibited recurrent symptoms of the non-invasive fungus-induced rhinosinusitis condition. Two other patients switched from an amphotericin B solution (duration: 3 months; frequency: twice a day) to an itraconazole solution (duration: 1 month; frequency: twice a day). One reported feeling better after using the itraconazole solution for only seven days. Taken together, these results indicate that antifungal agents can be used effectively to treat non-invasive fungus-induced rhinosinusitis.

TABLE II

Patient data collected during a one week period.

| Age | Duration (Ampho) | Frequency | Last Surgery | Steroid Therapy | Other Diseases | Endoscopy Score B | Endoscopy Score A | Symptom Score B | Symptom Score A |
|---|---|---|---|---|---|---|---|---|---|
| 59 | 3 mon[1] | 2× day | 2 mon | No | Asthma | NA | NA | −1 | 1 |
| 40 | 1 mon | 2× day | None | Yes[8] | Asthma Colitis | 2 | 1 | −1 | +2 |
| 63 | 4 mon | 1× day | 4 mon | No | Colitis | 1 | 0 | −1 | +1 |
| 16 | 12 mon[2] | 1× day | 26 mon | Topical | Asthma | 2 | 0 | −1 | +2 |
| 44 | 12 mon[2] | 2× day | 9 mon | No | Asthma | 3 | 0 | −1 | +1 |
| 40 | 2 mon[3] | 2× day | 12 mon | No | No | 3 | 3 | −1 | 0 |
| 23 | 16 mon | 2× day | 10 mon | No | Asthma | 3 | 0 | −1 | +1 |
| 48 | 4 mon | 2× day | >10 yrs | Topical | No | 2 | 0 | −1 | 0 |
| 50 | 4 mon | 2× day | 4 mon | No | Asthma | 1 | 0 | −1 | +1 |
| 45 | 2 mon | 2× day | None | Topical | Asthma | 1 | NA | −1 | 0 |
| 74 | 2 mon | 2× day | >4 yrs | Topical | No | 2 | NA | −1 | +1 |
| 57 | 2 mon | 2× day | 1 mon | Systemic Topical | Asthma | 2 | 0 | −1 | +2 |
| 16 | 12 mon[4] | 1× day | 12 mon | No | Asthma[12] | 3 | 0 | −1 | +2 |
| 71 | 7 mon | 2× day | >6 yrs | No | Asthma | 3 | 3 | −2 | −2 |
| 38 | 12 mon | 2× day | >6 yrs | Yes[9] | Asthma | 3 | 3 | −1 | 0 |
| 38 | 5 mon | 2× day | 28 mon | No | Asthma | 0 | 0 | −2 | +2 |
| 66 | 13 mon | 2× day | >4 yrs | Topical | No | 3 | 3 | −2 | 0 |
| 70 | 3 mon[5] | 2× day | >2 yrs | Systemic[10] Topical | Asthma | 3 | 3 | −2 | +1 |
| 32 | 3 mon[6] | 2× day | 5 mon | No | Asthma | 3 | 1 | −2 | +2 |
| 47 | 2 mon[7] | 2× day | >3 yrs | Systemic[11] Topical | Asthma | 3 | 0 | −2 | 0 |

B, before antifungal treatment; A, after antifungal treatment
[1]Also irrigated with Wilson's solution (80 mg gentamicin/L saline) twice a day
[2]Also intermittently irrigated with Wilson's solution
[3]Stopped the nasal irrigations 8 months earlier and disease has recurred
[4]Also irrigated with Wilson's solution (80 mg gentamicin/L saline) once a day
[5]Felt better seven days after switching from amphotericin B (duration: 3 months; frequency: twice a day) to itraconazole (duration: 1 month; frequency: twice a day) nasal irrigations
[6]Switched to itraconazole irrigations (duration: 1 month; frequency: twice a day) after 3 months on amphotericin B
[7]Also irrigated with Wilson's solution (duration: 1 year)
[8]Received Kenalog 40 IM Medval Dose Pack 1 month earlier
[9]Received Kenalog Shot 6 months earlier
[10]Received Prednisone for 1 week
[11]Received systemic steroid treatment for 3 years
[12]Quit taking theophylline and tylade since starting antifungal irrigations Example 3

Treating and Preventing Non-Invasive Fungus-Induced Rhinosinusitis in Patients Without Previous Nasal Surgery The following three non-invasive fungus-induced rhinosinusitis patients did not have a previous nasal surgery.

A 61 year old male was diagnosed with non-invasive fungus-induced rhinosinusitis and instructed to perform amphotericin B irrigations twice a day. Before starting the treatment, endoscopic evaluation revealed polyps filling her nasal cavity (endoscopic score 3) and the patient gave herself a symptom score of −1. After using the amphotericin B irrigations for fourteen months, endoscopic evaluation revealed no evidence of disease (endoscopic score 0) and the patient gave herself a symptom score of +2.

A 64 year old female was diagnosed with non-invasive fungus-induced rhinosinusitis and instructed to perform amphotericin B irrigations twice a day, which was later increased to four times a day. Before starting the treatment, endoscopic evaluation revealed evidence of polypoid changes (endoscopic score 1) and the patient gave himself a symptom score of −1. After using the amphotericin B irrigations for sixteen months, endoscopic evaluation revealed no evidence of disease (endoscopic score 0) and the patient gave himself a symptom score of +2.

A 54 year old male was diagnosed with non-invasive fungus-induced rhinosinusitis and instructed to perform amphotericin B irrigations twice a day. This patient had been given intramuscular steroid shots every 3 to 8 months with the last shot being administered about seven months prior to starting the amphotericin B irrigations. Before starting the antifungal treatment, endoscopic evaluation revealed no evidence of disease (endoscopic score 0) but the patient gave herself a symptom score of −1. After using the amphotericin B irrigations for four months, endoscopic evaluation again revealed no evidence of disease (endoscopic score 0), however, the patient gave herself a symptom score of +1.

Example 4

Diminishing Eosinophilia Using an Antifungal Treatment

A 67 year old female was diagnosed with non-invasive fungus-induced rhinosinusitis and instructed to perform amphotericin B irrigations twice a day. After nine months of amphotericin B irrigations, the patient underwent sinus surgery for further improvement. During the surgery mucosal biopsies were collected and the eosinophil count compared to the those obtained from biopsies collected from the patient during a surgery prior to the antifungal treatment.

The eosinophil count in all the mucosal biopsies from all the sinuses, except the frontal was diminished (<5%) after antifungal treatment. The eosinophil count in the frontal sinus biopsy was 10%. In addition, allergic mucus appeared to be present in the frontal sinus, presumably because the amphotericin B irrigations did not get to the frontal sinus due to the frontal sinus obstruction. Thus, the previously observed hypereosinophilia had diminished to normal in all the treated sinus areas.

Example 5

Treating and Preventing Chronic Asthma Symptoms

Thirty-seven of the 53 patients in the study described in Example 2 had previously diagnosed chronic asthma. After three months of antifungal treatment, 28 of the 37 asthmatic patients upon questioning declared an improvement or complete elimination of asthma symptoms. Four of these 28 were analyzed using a pulmonary function test after antifungal treatment since they had taken a similar test before antifungal treatment. Comparing the results before and after antifungal treatment confirmed that all four of these asthma patients had improved pulmonary function. In addition, 26 of the 28 patients no longer exhibiting asthma symptoms stopped taking their asthma medication. Twenty-three of these 26 patients were taking systemic steroids for asthma prior to the antifungal treatment, but none have subsequently taken steroids after starting the antifungal treatment.

In a separate study, sputum samples from the lung were collected from seven asthma patients. Culture analysis of these samples revealed the presence of fungal organisms in each sample. Specifically, *Candida albicans,* Penicillium, Fusarium, Scopulariopsis, Cryptococcus, Cladosporium, Aspergillus, *Aspergillus fumigatus, Aspergillus nidulans,* and yeast were cultured. The number of different fungal species cultured from each sputum sample ranged from one to five.

Example 6

Itraconazole Formulations

Itraconazole formulations were made by dissolving itraconazole into polyethylene glycol (PEG) to form an itraconazole stock solution. The itraconazole was obtained from 100 mg itraconazole capsules (Janssen Pharmaceutica, Inc.). Typically, PEG 400 was used to dissolve the itraconazole. Once dissolved, the stock solution was filtered to remove any insoluble material. Then, the stock solution was prepared for use by dilution with sterile water.

Specifically, twenty 100 mg itraconazole capsules were opened and the spheres having itraconazole were placed into a graduated cylinder. One liter of heated (70° C.) PEG-400 was added to the graduated cylinder containing the itraconazole. The mixture was then placed onto a stirring hot plate and maintained at 70° C. for 30 minutes. After 30 minutes, the hot suspension was filtered through a urine stone filter into a glass container and allowed to cool to room temperature. Once cooled, 100 mL of the filtered solution was placed into an empty plastic bottle. Then, 900 mL of sterile water was added and the solution mixed. Once mixed, one drop of flavoring was added (peppermint oil). This procedure typically resulted in a solution containing about 98.8 µg to about 111 µg of itraconazole per mL.

The following concentrations of itraconazole were determined for each indicated solution by HPLC (Table III).

TABLE III

Concentrations of itraconazole in solution.

| Solution | Soluble Itraconazole Concentration (µg/mL) |
|---|---|
| 2000 mg Itraconazole from capsules into 1 L PEG-400 (stock solution) | 1839 |
| 100 mL stock solution diluted with 900 mL sterile water | 113 |
| 500 mg Itraconazole powder "AS" into 250 mL PEG-400 (stock solution) | 1951 |
| 100 mL stock solution diluted with 900 mL sterile water | 85 |
| 2000 mg Itraconazole from capsules into 1 L PEG-400 (stock solution) | |
| 100 mL stock solution plus 150 mL PEG-400 diluted with 750 mL sterile water | 179 |
| 2000 mg Itraconazole from capsules into 1 L PEG-400 (stock solution) | |
| 100 mL stock solution plus 25 mL PEG-400 diluted with 875 mL sterile water | 155 |

An itraconazole formulation containing a steroid was also made. Specifically, the contents from two PULMICORT 200 µg inhalers (about 91 µg of budesonide total) was added to an itraconazole PEG-400 stock solution at 70° C. for about 15 minutes. The budesonide was added about 5 minutes after the itraconazole powder was dissolved into the PEG-400. After cooling to room temperature, some precipitation occurred. This insoluble material was removed by filtering the solution through fine filter paper under vacuum. The filter was dried and the captured precipitate was measured (36–40 µg). Thus, about 54 to 50 µg of steroid remained in the solution/fine suspension.

Example 7

Treating and Preventing Non-Invasive Fungus-Induced Rhinosinusitis Using Itraconazole Three non-invasive fungus-induced rhinosinusitis patients (33 year old male, 70 year male, and 57 year old female) were instructed to perform nasal irrigation with an itraconazole solution. The itraconazole solution contained about 100 mg of itraconazole per L of solution (10% PEG-400 in sterile water) and was prepared as described herein. Two patients were instructed to perform itraconazole irrigations because they did not respond to amphotericin B irrigations. Each patient reported marked improvement in symptoms within two weeks of starting the itraconazole irrigations (symptom scores: −1 to +2 and −1 to +1). Sixteen days after starting the itraconazole irrigations, one of these two patients exhibited improvement as revealed by endoscopic analysis (endoscopic score: from 1 to 0 for right side and from 1 to 1 for left side). In addition, this patient indicated that her asthma symptoms had dramatically improved and she reduced her asthma medication (Flovent and Servent) from twice a day to once a day.

The third patient was instructed to perform itraconazole irrigations because of an adverse local reaction to amphotericin B (burning sensation). After treatment with itraconazole, that patient reported symptom improvement (symptom score: from −1 to 0). In addition, that patient did not have any adverse local reaction or problems with the itraconazole irrigations.

Example 8

Treating and Preventing Chronic Asthma Symptoms Using Itraconazole

A 32 year old white male patient with no history or symptoms of chronic rhinosinusitis exhibited significant asthma symptoms despite medical therapy with systemic and topical steroids and frequent use of a bronchodilator. Sputum and nasal-paranasal mucus samples were collected and analyzed. Culture analysis revealed the presence of *Candida albicans* in the sputum and Penicillium, Geotrichum, Alternaria, and Cladosporium species in the nasal-paranasal mucus.

The patient was started on an antifungal treatment of about 20 mL of an itraconazole solution per nostril, two times daily. The concentration of the itraconazole solution was about 100 mg per liter. After a few weeks, the patient took his last course of systemic steroids. About two months after stopping the systemic steroids, the patient also stopped using the topical steroids as well as the bronchodilator. Since stopping all steroid therapy, the patient's symptoms improved dramatically. Specifically, the patient reports no episodes of shortness of breath and no wheezing during the four to five month period since stopping all steroid therapy.

Objective analysis also revealed dramatic improvement. In a study conducted before antifungal treatment, the patient exhibited abnormal pulmonary function. After seven months of continuous antifungal irrigations as described with the later four to five months being free of all steroid therapy, the patient exhibited improved pulmonary function. Specifically, the forced vital capacity (FVC) of the lung improved from 3.99 liter before treatment to 4.80 liter after treatment, an increase of 20.30%; the forced expiratory volume in 1 second (FEV1), a marker for the degree of lower airway resistance, improved from 3.34 liter before treatment to 4.27 liter after treatment, an increase of 27.84%; the maximal forced expiratory flow (FEFmax) improved from 9.1 liter per second before treatment to 12.6 liter per second after treatment, an increase of 38.46%; and the maximum voluntary ventilation (MVV) improved from 119 liter per minute before treatment to 156 liter per minute after treatment, an improve of 31.90%.

In summary, the objective markers revealed an improvement of the pulmonary function between 20.3% and 38.46%, despite no medical therapy other than the antifungal nasal irrigations during the previous four to five months. These results indicate that chronic asthma symptoms can be treated and prevented by mucoadministering antifungal agents to the airways.

Sometime after this patient's asthma symptoms improved, the patient stopped using the itraconazole irrigations. After four to six weeks of not using the itraconazole irrigations, the patient's asthma symptoms returned. At that time, the patient inhaled steroids only to control the asthma symptoms. After about four to six weeks, the patient switched from using the steroid inhaler to using an itraconazole powder inhaler. Specifically, the patient was instructed to inhale about 400 µg of pure itraconazole per day using a powdered inhaler. The itraconazole powder was an authentic substance "AS" (Janssen Pharmaceutica, Inc.). The inhaler was a Pulmicort 200 µg TURBOHALER® manufactured by ASTRA pharmaceuticals. This inhaled was designed for metered doses of budesonide inhalation powder, but was adapted to administer itraconazole. The patient has been asymptomatic for four weeks, and continues to use the itraconazole powdered treatment. The patient also had at least one nasal polyp initially. That polyp was noticeably reduced in viability by the second week of treatment.

Another asthma patient also was instructed to inhale about 200 µg of pure itraconazole per day using an adapted Pulmicort 200 µg TURBOHALER®. After about 2 weeks, the patient's condition was markedly improved. The patient remains on the treatment.

An asthma patient having non-invasive fungus-induced rhinosinusitis was treated with itraconazole using a nebulizer. Specifically, about two mL of an itraconazole solution (about 10 mg itraconazole per mL PEG-400) was applied per day in a nebulizer. The nebulizer was an air pressurized PULMO-MATE brand manufactured by DeVillbis. After about two weeks, the patient demonstrated improvement in both asthma and non-invasive fungus-induced rhinosinusitis conditions as evidenced by an overall improvement of symptom scores. Improvements were also noted in one week increments.

Example 9

Identifying Non-Invasive Fungus-Induced Otitis Media

Mucus samples from the middle ear were collected using a suction trap from three patients diagnosed with chronic otitis media. Culture analysis of the samples revealed the presence of fungal organisms. Specifically, the mucus sample from the first patient was positive for Candida and *Trichophyton rubrum* species, the mucus sample from the second patient was positive for Penicillium species, and the mucus sample from the third patient was positive for Aspergillus species. In addition, microscopic examination revealed a large number of degenerating eosinophils within each mucus sample. Thus, these results indicate that chronic otitis media is most likely caused by non-invasive fungal organisms. Moreover, it appears that chronic otitis media is a non-invasive fungus-induced mucositis that can be treated and prevented using the antifungal treatment and prevention approaches described herein.

Example 10

Treating Non-Invasive Fungus-Induced Intestinal Mucositis

Three out of five consecutive patients with chronic rhinosinusitis reported having a history of colitis. Two patients were started on an antifungal treatment of one capsule of itraconazole (provided by Janssen Pharmaceutica, Inc.) per day. The capsule contained 100 mg of itraconazole. Each patient was instructed to take the capsule before bedtime a minimum of two hours after their last meal and without any cola. Food and cola beverages increase absorption of the drug. When taken as described, about 50 percent of the itraconazole should remain in the bowel lumen for treatment of non-invasive fungus-induced intestinal mucositis symptoms.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for treating a mammal having non-invasive fungus-induced rhinosinusitis comprising the presence of allergic mucus, said method comprising directly mucoadministering to at least a portion of the nasal-paranasal anatomy of said mammal a formulation in an amount, at a frequency, and for a duration effective to reduce or eliminate said non-invasive fungus-induced rhinosinusitis, said formulation comprising an antifungal agent.

2. The method of claim 1, wherein said mammal is a human.

3. The method of claim 1, wherein said mammal is nonatopic.

4. The method of claim 1, wherein said mammal is immunocompetent.

5. The method of claim 1, wherein said non-invasive fungus-induced rhinosinusitis comprises polyp formation or polypoid change.

6. The method of claim 1, wherein said non-invasive fungus-induced rhinosinusitis is chronic.

7. The method of claim 1, wherein said formulation is in a liquid or aerosol form.

8. The method of claim 1, wherein said formulation is in a solid or aerosol form.

9. The method of claim 1, wherein said direct mucoadministration comprises irrigating said nasal-paranasal anatomy with a liquid form of said formulation.

10. The method of claim 1, wherein said direct mucoadministration comprises applying an aerosol form of said formulation to said nasal-paranasal anatomy.

11. The method of claim 1, wherein said direct mucoadministration comprises applying a powder form of said formulation to said nasal-paranasal anatomy.

12. The method of claim 1, wherein said antifungal agent comprises a macrolide.

13. The method of claim 1, wherein said antifungal agent comprises an azole.

14. The method of claim 1, wherein said antifungal agent interpolates fungal cell wall components.

15. The method of claim 1, wherein said antifungal agent comprises a sterol inhibitor.

16. The method of claim 1, wherein said antifungal agent comprises an antifungal agent selected from the group consisting of amphotericin B, ketoconazole, itraconazole, saperconazole, voriconazole, flucytosine, miconazole, fluconazole, griseofulvin, clotrimazole, econazole, terconazole, butoconazole, oxiconazole, sulconazole, ciclopirox olamine, haloprogin, tolnaftate, naftifine, terbinafine hydrochloride, morpholines, nystatin, natamycin, butenafine, undecylenic acid, Whitefield's ointment, propionic acid, and caprylic acid.

17. The method of claim 1, wherein said antifungal agent comprises an antifungal agent selected from the group consisting of amphotericin B, ketoconazole, itraconazole, saperconazole, and voriconazole.

18. The method of claim 1, wherein said antifungal agent comprises amphotericin B.

19. The method of claim 1, wherein said antifungal agent comprises itraconazole.

20. The method of claim 1, wherein said formulation comprises a pharmaceutically acceptable aqueous vehicle.

21. The method of claim 20, wherein said formulation comprises about 0.01 ng to about 1000 mg of said antifungal agent per liter.

22. The method of claim 21, wherein said effective amount comprises about 0.01 mL to about 1 L of said formulation per nostril of said mammal.

23. The method of claim 21, wherein said effective amount comprises about 5 mL to about 100 mL of said formulation per nostril of said mammal.

24. The method of claim 21, wherein said effective amount comprises about 20 mL of said formulation per nostril of said mammal.

25. The method of claim 20, wherein said formulation comprises about 1 ng to about 500 mg of said antifungal agent per liter.

26. The method of claim 20, wherein said formulation comprises about 100 mg of said antifungal agent per liter.

27. The method of claim 1, wherein said formulation comprises a plurality of antifungal agents.

28. The method of claim 1, wherein said effective amount of said formulation comprises about 0.01 ng to about 1000 mg of said antifungal agent per kg of body weight of said mammal.

29. The method of claim 1, wherein said effective amount of said formulation comprises about 1 ng to about 500 mg of said antifungal agent per kg of body weight of said mammal.

30. The method of claim 1, wherein said effective amount of said formulation remains constant during said effective duration.

31. The method of claim 1, wherein said effective frequency of said direct mucoadministration is from about four times a day to about once every other week.

32. The method of claim 1, wherein said effective frequency of said direct mucoadministration is from about twice a day to about once a week.

33. The method of claim 1, wherein said effective frequency of said direct mucoadministration is more frequent than once a day.

34. The method of claim 1, wherein said effective frequency of said direct mucoadministration is more frequent than once a week.

35. The method of claim 1, wherein said effective duration is greater than about 7 days.

36. The method of claim 1, wherein said effective duration is greater than about 14 days.

37. The method of claim 1, wherein said effective duration is greater than about 30 days.

38. The method of claim 1, wherein said effective duration is greater than about 60 days.

39. The method of claim 1, wherein said effective duration is greater than about 90 days.

40. The method of claim 1, wherein said formulation further comprises a compound selected from the group consisting of pharmaceutically acceptable aqueous vehicles, pharmaceutically acceptable solid vehicles, mucolytic agents, antibacterial agents, anti-inflammatory agents, immunosuppressants, dilators, vaso-constrictors, and steroids.

41. The method of claim 1, wherein said method further comprises administering to said mammal a second formulation, said second formulation comprising a compound selected from the group consisting of antifungal agents, pharmaceutically acceptable aqueous vehicles, pharmaceutically acceptable solid vehicles, mucolytic agents, antibacterial agents, anti-inflammatory agents, immunosuppressants, dilators, vaso-constrictors, and steroids.

42. The method of claim 1, said method comprising, after said direct mucoadministration, prophylactically mucoadministering to said mammal a prophylactic formulation in an amount, at a frequency, and for a duration effective to prevent said non-invasive fungus-induced rhinosinusitis, said prophylactic formulation comprising an antifungal agent.

43. The method of claim 42, wherein said prophylactic mucoadministration comprises direct mucoadministration.

44. The method of claim 1, wherein said mucoadministration begins during a period noncoincident with an intraoperative period, said intraoperative period being the time during a nasal surgery.

45. The method of claim 44, wherein said mammal had a nasal surgery before said mucoadministration.

46. The method of claim 44, wherein said mammal was nasal surgery-free before said mucoadministration.

* * * * *

UNITED STATES PATENT AND TRADEMARK OFFICE
CERTIFICATE OF CORRECTION

PATENT NO. : 6,555,566 B2
DATED : April 29, 2003
INVENTOR(S) : Ponikau, Jens

It is certified that error appears in the above-identified patent and that said Letters Patent is hereby corrected as shown below:

Title page,
Item [56], References Cited, OTHER PUBLICATIONS, "Birnbaum et al." reference, "Sermatol." should read -- Dermatol. --.

Signed and Sealed this

Eighth Day of June, 2004

JON W. DUDAS
*Acting Director of the United States Patent and Trademark Office*